(12) United States Patent
Davis et al.

(10) Patent No.: US 11,439,796 B2
(45) Date of Patent: Sep. 13, 2022

(54) INFLATION DEVICES WITH PROXIMITY PAIRING AND METHODS AND SYSTEMS RELATED THERETO

(71) Applicant: Merit Medical Systems, Inc., South Jordan, UT (US)

(72) Inventors: Jon Davis, Sandy, UT (US); Tamara Smith Duncan, Saratoga Springs, UT (US); David Mandel, Alexandria, VA (US); Christopher Rice, Alexandria, VA (US); Zachary Glickstein, Alexandria, VA (US); Christopher Hile, Springfield, VA (US); Jeremy Mushailov, Washington, DC (US)

(73) Assignee: Merit Medical Systems, Inc., South Jordan, UT (US)

( * ) Notice: Subject to any disclaimer, the term of this patent is extended or adjusted under 35 U.S.C. 154(b) by 633 days.

(21) Appl. No.: 16/393,467

(22) Filed: Apr. 24, 2019

(65) Prior Publication Data
US 2019/0329008 A1 Oct. 31, 2019

Related U.S. Application Data

(60) Provisional application No. 62/663,035, filed on Apr. 26, 2018.

(51) Int. Cl.
*A61M 25/10* (2013.01)
*A61M 25/00* (2006.01)

(52) U.S. Cl.
CPC ............ *A61M 25/10187* (2013.11); *A61M 2025/0002* (2013.01); *A61M 2205/3331* (2013.01); *A61M 2205/35* (2013.01); *A61M 2205/587* (2013.01)

(58) Field of Classification Search
CPC ...... A61M 25/10188; A61M 25/10182; A61M 25/10187; A61M 2205/587;
(Continued)

(56) References Cited

U.S. PATENT DOCUMENTS

D309,663 S 7/1990 Robinson
D330,078 S 10/1992 Porter
(Continued)

FOREIGN PATENT DOCUMENTS

JP 2017225725 12/2017
WO 2011097487 8/2011
(Continued)

OTHER PUBLICATIONS

Office Action dated Apr. 27, 2021 for U.S. Appl. No. 16/557,516.
(Continued)

*Primary Examiner* — Nathan R Price
*Assistant Examiner* — Anh Bui
(74) *Attorney, Agent, or Firm* — Dorsey & Whitney LLP

(57) ABSTRACT

Inflation devices configured to communicate with remote displays are disclosed herein. Systems including such inflation devices with portable display devices are also disclosed herein. Methods of pairing a medical device to a portable display and remotely displaying pressure data from a medical device are also disclosed herein. Devices, systems, and methods of connecting medical devices to remote displays using proximity pairing and visual aids, and transferring information to or from linked computers are also disclosed.

20 Claims, 12 Drawing Sheets

(58) Field of Classification Search
CPC ...... A61M 2205/35; A61M 2205/3331; A61M 2025/0002
See application file for complete search history.

(56) References Cited

U.S. PATENT DOCUMENTS

| | | | |
|---|---|---|---|
| D330,763 S | 11/1992 | Penny | |
| D331,107 S | 11/1992 | Kanner | |
| 5,201,753 A | 4/1993 | Lampropoulos et al. | |
| 5,215,523 A | 6/1993 | Williams et al. | |
| 5,259,838 A | 11/1993 | Taylor et al. | |
| 5,318,533 A | 6/1994 | Adams et al. | |
| 5,383,855 A | 1/1995 | Nicholson et al. | |
| 5,387,194 A | 2/1995 | Williams et al. | |
| 5,449,345 A | 9/1995 | Taylor et al. | |
| 5,453,091 A | 9/1995 | Taylor et al. | |
| 5,562,621 A | 10/1996 | Claude et al. | |
| 5,647,847 A | 7/1997 | Lafontaine et al. | |
| 5,695,466 A | 12/1997 | Lopez et al. | |
| 6,139,523 A | 10/2000 | Taylor et al. | |
| D439,584 S | 3/2001 | Wang | |
| D440,575 S | 4/2001 | Wang | |
| 6,377,848 B1 | 4/2002 | Garde et al. | |
| 6,389,143 B1 | 5/2002 | Leedom et al. | |
| 6,394,977 B1 | 5/2002 | Taylor et al. | |
| D523,871 S | 6/2006 | Hally | |
| D524,321 S | 7/2006 | Hally | |
| D525,984 S | 8/2006 | Hally | |
| D528,124 S | 9/2006 | Hally | |
| D528,559 S | 9/2006 | Hally | |
| D534,916 S | 1/2007 | Hone | |
| D537,449 S | 2/2007 | Hoefnagels | |
| D550,691 S | 9/2007 | Hally | |
| 7,351,223 B2 | 4/2008 | Call | |
| D601,156 S | 9/2009 | Motohashi | |
| D606,085 S | 12/2009 | Agnetta | |
| D627,365 S | 11/2010 | Brinda | |
| 7,892,202 B2 | 2/2011 | Lampropoulos et al. | |
| D676,060 S | 2/2013 | Frost | |
| D687,058 S | 7/2013 | Corcoran | |
| D690,318 S | 9/2013 | Kluttz | |
| D690,322 S | 9/2013 | Matas | |
| D696,677 S | 12/2013 | Corcoran | |
| D697,519 S | 1/2014 | Thomsen | |
| D701,226 S | 3/2014 | Jung | |
| D701,869 S | 4/2014 | Matas | |
| D702,723 S | 4/2014 | Abratowski | |
| D709,913 S | 7/2014 | Hurd | |
| D714,931 S | 10/2014 | Sealfon | |
| 8,915,891 B2 | 12/2014 | Bornhoft | |
| D722,082 S | 2/2015 | Roberts | |
| D727,354 S | 4/2015 | Park | |
| D727,495 S | 4/2015 | Bown | |
| 9,058,696 B2 | 6/2015 | Omiya | |
| D740,300 S | 10/2015 | Lee | |
| D741,356 S | 10/2015 | Park | |
| D742,898 S | 11/2015 | Matas | |
| D748,126 S | 1/2016 | Sarukkai | |
| D749,092 S | 2/2016 | Lee | |
| 2004/0122369 A1 | 6/2004 | Schriver et al. | |
| 2004/0176984 A1 | 9/2004 | White et al. | |
| 2004/0260238 A1 | 12/2004 | Call | |
| 2005/0148869 A1 | 7/2005 | Masuda | |
| 2007/0112299 A1 | 5/2007 | Smit et al. | |
| 2007/0213656 A1 | 9/2007 | Ferdinand | |
| 2007/0266344 A1 | 11/2007 | Olcott | |
| 2008/0086087 A1 | 4/2008 | Spohn et al. | |
| 2008/0250340 A1* | 10/2008 | Dlugos ................ A61B 5/002 715/771 |
| 2009/0281489 A1 | 11/2009 | Lampropoulos et al. | |
| 2010/0217188 A1 | 8/2010 | Lampropoulos et al. | |
| 2010/0274180 A1 | 10/2010 | Donovan et al. | |
| 2011/0144419 A1 | 6/2011 | Timm et al. | |
| 2011/0238082 A1 | 9/2011 | Wenderow et al. | |
| 2012/0116366 A1 | 5/2012 | Houser et al. | |
| 2013/0132028 A1 | 5/2013 | Crankson | |
| 2013/0132887 A1 | 5/2013 | Amin | |
| 2013/0197679 A1 | 8/2013 | Balakrishnan | |
| 2013/0310753 A1 | 11/2013 | Cabiri | |
| 2013/0310756 A1* | 11/2013 | Whalley ............. A61M 5/3129 604/189 |
| 2013/0324989 A1 | 12/2013 | Leung | |
| 2013/0331634 A1 | 12/2013 | Kaintz et al. | |
| 2014/0045010 A1 | 2/2014 | Myers et al. | |
| 2014/0275935 A1 | 9/2014 | Walsh et al. | |
| 2015/0038901 A1 | 2/2015 | Lampropoulos et al. | |
| 2015/0088091 A1 | 3/2015 | Beasley et al. | |
| 2015/0141915 A1 | 5/2015 | Lampropoulos et al. | |
| 2015/0193553 A1 | 7/2015 | Petersen | |
| 2016/0239610 A1* | 8/2016 | Andersen ............ A61M 5/3202 |
| 2017/0140120 A1 | 5/2017 | Thrower | |
| 2017/0201811 A1* | 7/2017 | Tateda ................. A61B 5/6826 |
| 2017/0368248 A1* | 12/2017 | Neftel ................. G06F 9/30003 |
| 2019/0251354 A1* | 8/2019 | Cork ....................... G06F 3/167 |
| 2020/0061353 A1 | 2/2020 | Lampropoulos et al. | |
| 2020/0261629 A1* | 8/2020 | Hunt ....................... A61M 1/90 |

FOREIGN PATENT DOCUMENTS

| | | |
|---|---|---|
| WO | 2011119896 | 9/2011 |
| WO | 2015020895 | 2/2015 |
| WO | 2016123052 A1 | 8/2016 |
| WO | 2019209964 | 10/2019 |

OTHER PUBLICATIONS

International Search Report and Written Opinion dated Oct. 30, 2019 for PCT/US2019/028931.
European Search Report dated Mar. 15, 2017 for EP148341993.
European Search Report dated Mar. 22, 2019 for EP14834199.3.
European Search Report dated Jul. 3, 2018 for EP16759456.3.
European Search Report dated Aug. 23, 2018 for EP16743928.0.
International Search Report and Written Opinion dated May 12, 2016 for PCT/US2016014822.
International Search Report and Written Opinion dated Jun. 14, 2016 for PCT/US2016/020574.
International Search Report and Written Opinion dated Nov. 11, 2014 for PCT/US2014/049364.
Notice of Allowance dated Jan. 21, 2016 for U.S. Appl. No. 29/504,961.
Notice of Allowance dated Mar. 18, 2016 for U.S. Appl. No. 29/504,954.
Notice of Allowance dated Apr. 13, 2016 for U.S. Appl. No. 29/504,954.
Notice of Allowance dated May 7, 2018 for U.S. Appl. No. 15/059,545.
Notice of Allowance dated Jun. 6, 2018 for U.S. Appl. No. 14/608,904.
Notice of Allowance dated Jun. 27, 2016 for U.S. Appl. No. 29/504,937.
Office Action dated Feb. 13, 2018 for U.S. Appl. No. 14/449,506.
Office Action dated Feb. 23, 2016 for U.S. Appl. No. 29/504,937.
Office Action dated Feb. 25, 2019 for U.S. Appl. No. 14/449,506.
Office Action dated Aug. 27, 2018 for U.S. Appl. No. 14/449,506.
Office Action dated Sep. 25, 2017 for U.S. Appl. No. 14/608,904.
Office Action dated Sep. 26, 2017 for U.S. Appl. No. 14/449,506.
Notice of Allowance dated Oct. 29, 2021 for U.S. Appl. No. 16/557,516.

* cited by examiner

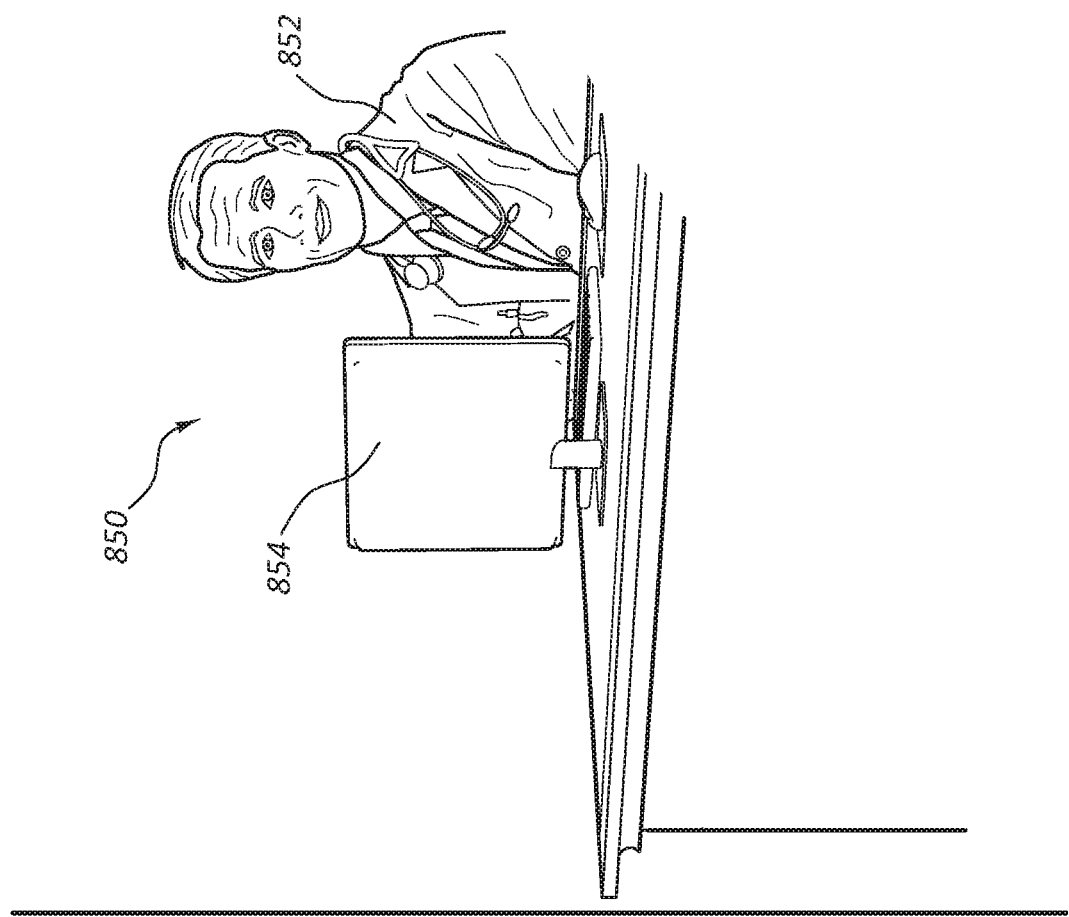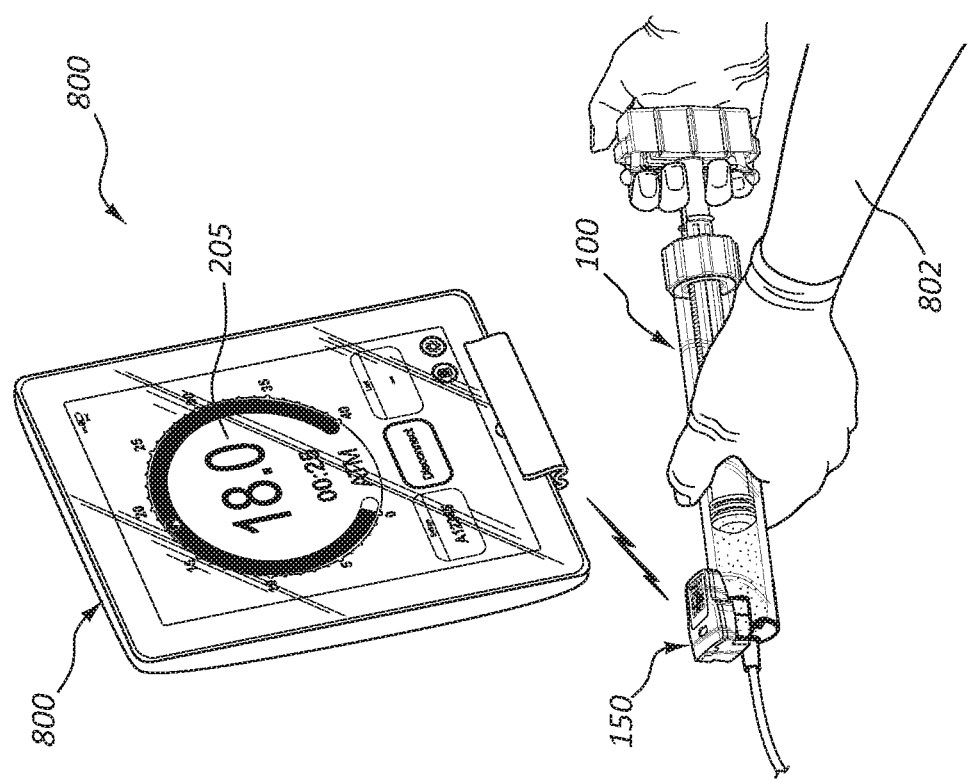
FIG. 8

INFLATION DEVICES WITH PROXIMITY PAIRING AND METHODS AND SYSTEMS RELATED THERETO

RELATED CASES

This application claims priority to U.S. Provisional Application No. 62/663,035, filed on Apr. 26, 2018 and titled "INFLATION DEVICES WITH PROXIMITY PAIRING AND METHODS AND SYSTEMS RELATED THERETO" which is hereby incorporated by reference in its entirety.

TECHNICAL FIELD

The present disclosure relates generally to devices used to pressurize, depressurize, or otherwise displace fluid, particularly in medical devices. More specifically, the present disclosure relates to remote displays for inflation devices.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 8 illustrates an inflation device used with two remote display devices.

DETAILED DESCRIPTION

Figure 1:
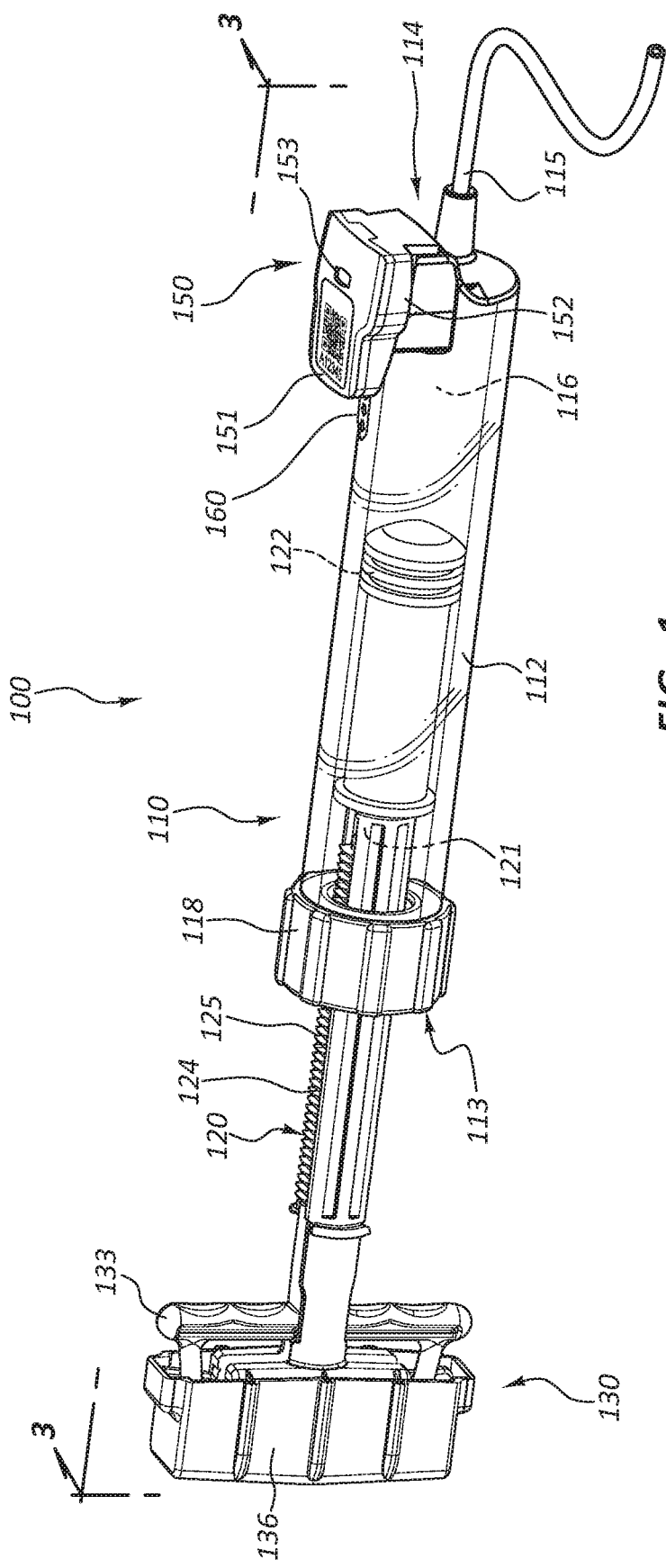
FIG. 1 is a perspective view of an inflation device with a pressure sensor and a wireless transmitter with proximity pairing.

Inflation devices configured for use in connection with a medical device are disclosed herein. The inflation devices may comprise a body component and a pressurization component configured to increase or decrease pressure within the body component by displacing the pressurization component with respect to the body component. The inflation devices may further comprise an actuator operably connected to the pressurization component and configured to displace the body component.

Inflation devices may be used to pressurize and deliver fluid. "Fluid" is used in its broadest sense, to refer to any fluid, including both liquids and gases as well as solutions, compounds, suspensions, etc., that generally behave as fluids. Thus, inflation devices within the scope of this disclosure may be used, for example, for pressurizing a balloon or delivering bone cement.

One or more sensors may measure characteristics associated with the inflation device and/or liquid being delivered by the inflation device. A pressure sensor may be in communication with the body component and configured to measure pressure within the body component. A temperature sensor may be configured to measure room temperature or a temperature of a liquid being delivered by the inflation device. A volume sensor may track displacement of the pressurization component to determine an amount of liquid displaced by the inflation device.

A transmitter may be in communication with the sensors and configured to transmit a wireless signal containing measurements of the sensors. For example, the wireless signal may contain the pressure measured by the pressure sensor, the temperature measured by the temperature sensor, and the amount of liquid displaced measured by the volume sensor.

Inflation systems are also disclosed herein. The systems may comprise an inflation device disclosed herein and a portable display device configured to receive the wireless signal transmitted by the inflation device transmitter and also configured to display data from the sensors, such as real-time pressure data within the body component. In some embodiments, two portable display devices may display data from the sensors.

Methods of pairing the inflation device to the portable display and displaying sensor data are also disclosed herein. The methods may comprise capturing an image stream with a camera, displaying the image stream on the portable display, overlaying a frame on the image stream for alignment of the portable display with the medical device for pairing, measuring a signal from the medical device, and pairing the remote display device with the medical device when the signal strength exceeds a threshold signal strength.

It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with," refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component. With regard to wireless transfer of data between components which are wirelessly connected, coupled, or in communication with each other, any form of wireless interaction, including radio communication, optical communication, Bluetooth communication, Wi-Fi communication, infrared communication, sound wave transfer, and so forth are all within the scope of this disclosure.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

Figure 2:
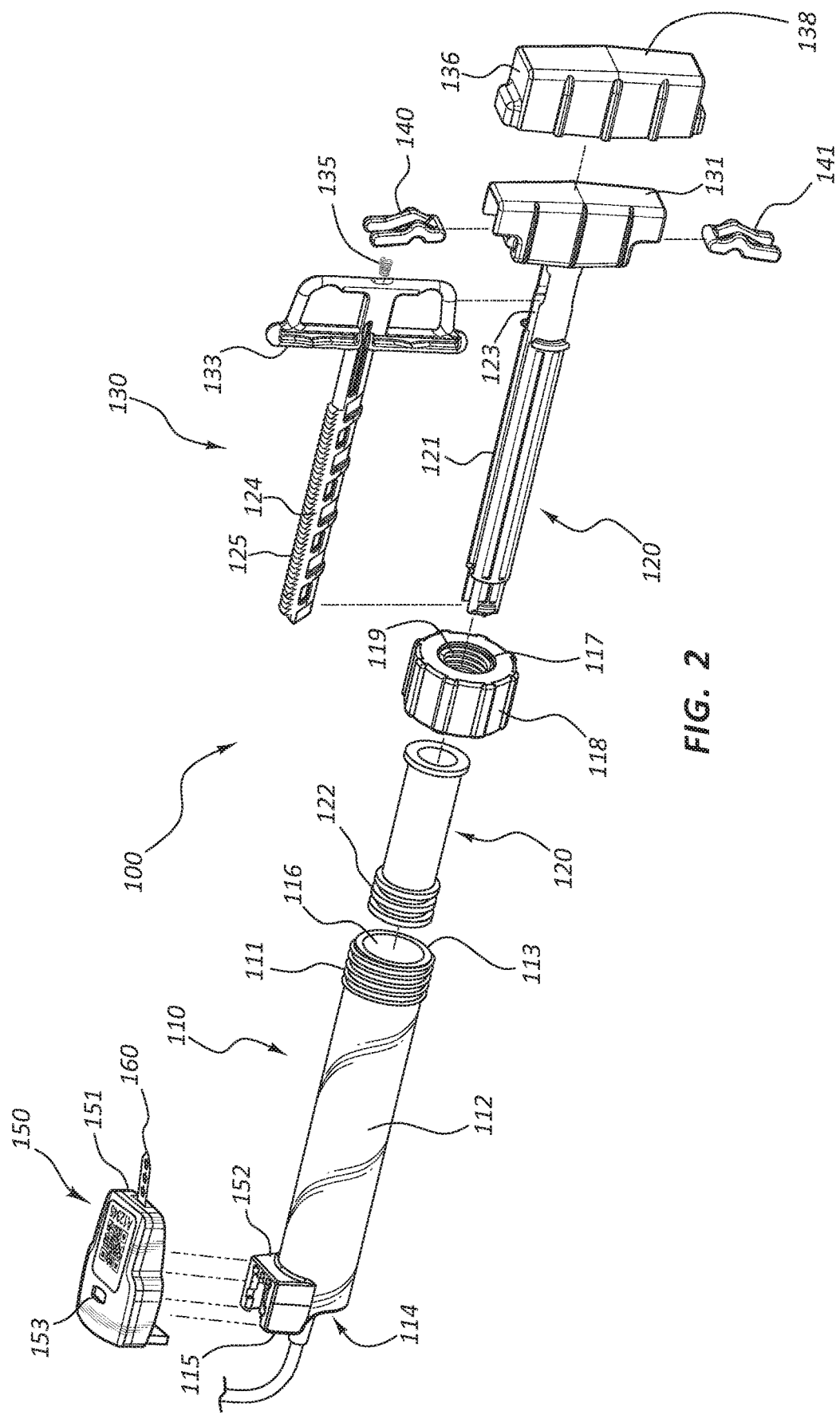
FIG. 2 is an exploded view of the inflation device of FIG. 1.
Figure 3:
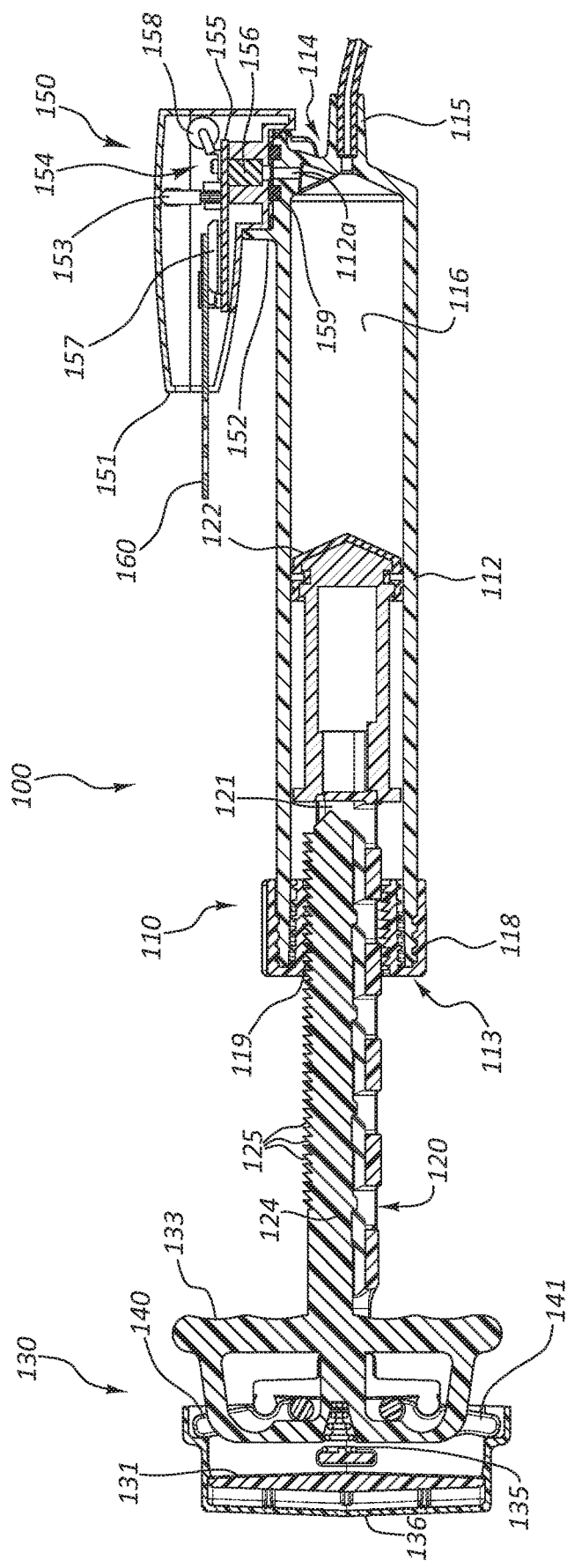
FIG. 3 is a cross sectional view of the inflation device of FIG. 1 taken through plane 3-3.

FIGS. 1-3 illustrate different views of an inflation device with a pressure sensor and a wireless transmitter. In certain views the device may be coupled to, or shown with, additional components not included in every view. In some views only selected components are illustrated, to provide detail regarding the relationship of the components. Some components may be shown in multiple views but not discussed in connection with every view. Disclosure provided in connection with any figure is relevant and applicable to disclosure provided in connection with any other figure. The devices, kits, and methods disclosed herein may be applicable to a variety of medical procedures, including inflation sequences, injection sequences, and so forth. Any concepts disclosed herein in connection with any particular procedure may be analogously applied to other medical procedures as well.

FIG. 1 is a perspective view of an inflation device 100. In the illustrated embodiment, the inflation device 100 is partially comprised of a syringe 110. The inflation device 100 includes four broad groups of components; each group may have numerous subcomponents and parts. The four broad component groups are: a body component such as a syringe body 112, a pressurization component such as a plunger 120, a handle 130, and a sensor component 150.

Referring to FIGS. 1-3, the sensor component 150 comprises a pressure sensor 156 and a transmitter 158. The transmitter 158 may be configured to transmit radio waves. For example, the transmitter 158 may be configured as a Bluetooth transmitter and/or as a Wi-Fi transmitter. In some instances, Bluetooth transmission may result in less power consumption of the transmitter 158 than that of a Wi-Fi transmitter. The transmitter 158 may also be configured to transmit other forms of electromagnetic radiation instead of radio waves, such as, for example, infrared light. Still further, the transmitter 158 may be configured to transmit other waves or signals, for example, sound waves.

The transmitter 158 may be configured to allow for wireless remote display of pressure signals generated by the pressure sensor 156. The ability to have a remote display may facilitate a doctor's utilization an inflation device. For example, in many procedures, space in the immediate vicinity of a patient's body during a medical procedure is at a premium, particularly the space near the insertion site of a catheter during an interventional procedure. When an inflation device is close to the insertion site, a display mounted on the inflation device may obscure a user's view of the insertion site and may block access to the insertion site by surgical staff. Additionally, a display mounted on an inflation device may only be visible to the individual using the inflation device.

In procedures and systems comprising a transmitter 158, a signal representative of pressure data may be sent to a remote display device located in the operating room. The remote display device may then be placed away from the insertion site, thereby allowing a user of the inflation device a clear view of any stress being placed on the insertion site by a catheter or pressurization line. The remote display device may be located so as to not block access to the insertion site by surgical staff. Also, the remote display device may be located so as to be clearly visible to other surgical staff. This may allow multiple individuals to be aware of the pressure conditions of a medical device within the patient. This knowledge may in turn assist surgical staff to work as a team instead of waiting for instructions from the user of the inflation device.

The remote display may comprise a portable display. Any exemplary references herein to a portable display may be applied to any remote display, for example, desktop computers, fixed display screens, tablet computers, portable display screens, and so forth.

The syringe body 112 may be formed of a generally cylindrical hollow tube configured to receive the plunger 120. The syringe body 112 may include an inlet/outlet port 115 located adjacent a distal end 114 of the syringe body 112. In some embodiments, a coupling member 118 is coupled to the syringe body 112 adjacent a proximal end 113 of the syringe body 112. The coupling member 118 may include a center hole configured to allow the plunger 120 to pass through the coupling member 118 into the syringe body 112. Further, the coupling member 118 may include coupling member threads 119 (FIG. 2) configured to selectively couple the coupling member 118 to the plunger 120.

The plunger 120 may be configured to be longitudinally displaceable within the syringe body 112. The plunger 120 may be comprised of a plunger shaft 121 coupled to a plunger seal 122 at the distal end of the plunger shaft 121. The plunger shaft 121 may also be coupled to the handle 130 at the proximal end of the plunger shaft 121, with the plunger shaft 121 spanning the distance between the plunger seal 122 and the handle 130.

The handle 130 broadly refers to the group of components coupled to the proximal end of the plunger 120, some of which may be configured to be graspable by a user. In certain embodiments, the handle 130 is configured such that the user can manipulate the position of the plunger 120 by manipulating the handle 130. Further, in some embodiments, the handle 130 is an actuator mechanism configured to manipulate components of the inflation device 100.

Components disclosed in connection with any of the exemplary handle configurations herein may be optional. That is, though the handle 130 broadly refers to the components coupled to the proximal end of the plunger shaft 121 that may be configured to be graspable by a user, use of the term "handle" is not meant to indicate that every disclosed handle component is always present. Rather, the term is used broadly, referring to the collection of components, but not specifically referring to or requiring the inclusion of any particular component. Likewise, other broad groupings of components disclosed herein, such as the syringe 110 or syringe body 112 and the plunger 120, may also refer to collections of individual subcomponents. Use of these terms should also be considered non-limiting, as each subcomponent may or may not be present in every embodiment.

As shown in FIG. 1, a fluid reservoir 116 may be defined by the space enclosed by the inside walls of the syringe body 112 between the plunger seal 122 and the distal end 114 of the syringe body 112. Accordingly, movement of the plunger seal 122 with respect to the syringe body 112 alters the size and volume of the reservoir 116.

As shown in FIGS. 1 and 2, in some embodiments, the syringe 110 includes the coupling member 118, fixedly coupled to the proximal end 113 of the syringe body 112. The coupling member 118 may utilize threads 117 or other coupling mechanisms to fixedly couple the coupling member 118 to corresponding threads 111 on the syringe body 112. The coupling member 118 may additionally include the coupling member threads 119 configured to couple the coupling member 118 to a portion of the plunger 120. The plunger 120 may also include external plunger threads 125 configured to couple the plunger 120 to the coupling member 118. The plunger 120 may thus be translated longitudinally with respect to the syringe body 112 by rotating the plunger 120 such that the interaction of the coupling member threads 119 and the plunger threads 125 results in the longitudinal translation of the plunger 120. Thus, when the plunger threads 125 and the coupling member threads 119 are engaged, movement of the plunger 120 is constrained with respect to the syringe body 112, though the plunger 120 is not necessarily fixed with respect to the syringe body 112. For example, the plunger 120 may be rotatable, but not directly translatable, when the threads 125, 119 are engaged.

The plunger threads 125 may be configured such that they may be retracted within the plunger shaft 121. As shown in FIG. 3, in some embodiments, the plunger threads 125 do not extend 360 degrees around the axis of the plunger shaft 121. Furthermore, as shown in FIGS. 2 and 3, the plunger threads 125 may be formed on a thread rail 124, which may be disposed within a groove 123 in the plunger shaft 121.

Translation of the thread rail 124 in the proximal direction simultaneously causes the thread rail 124 to retract toward the center axis of the plunger shaft 121. Similarly, translation of the thread rail 124 in the distal direction causes the thread rail 124 to move away from the center axis of the plunger shaft 121 and toward coupling member threads 119 of the coupling member 118. In the illustrated embodiment, a distally oriented biasing force acting on the thread rail 124 biases the plunger threads 125 to the engaged position. Operation of the coupling member 118 and the thread rail 124 is further discussed in U.S. Patent Publication No. 2013-0123693, the contents of which are incorporated herein by reference in their entirety.

It will be appreciated by one of ordinary skill in the art having the benefit of this disclosure that it is within the scope of this disclosure to modify the angles and interfaces such that a distally oriented biasing force on the thread rail 124 would bias the plunger threads 125 in the retracted position. Analogous mechanisms are disclosed in U.S. Pat. Nos. 5,047,015, 5,057,078, 5,163,904, and 5,209,732, which are each incorporated by reference in their entireties.

The retractable threads may allow a user to displace the plunger shaft 121 relative to the syringe body 112 either through rotation of the plunger shaft 121 (and the subsequent interaction of threads), or by retracting the plunger threads 125 and displacing the plunger shaft 121 by applying opposing forces on the plunger shaft 121 and the syringe body 112. (The forces, of course, may move the plunger shaft 121 distally or proximally with respect to the syringe body 112.) Both methods of displacement may be utilized during the course of a single therapy.

In some instances, a practitioner may desire to quickly displace the plunger shaft 121, for instance, while priming the inflation device 100 or while priming or deflating an attached medical device such as a balloon. Quick displacement of the plunger shaft 121 may be accomplished by retracting the plunger threads 125 and sliding the plunger shaft 121 relative to the syringe body 112. For example, a practitioner may quickly fill the reservoir 116 with fluid by disengaging the plunger threads 125 and pulling the plunger shaft 121 in a proximal direction with respect to the syringe body 112. Further, a practitioner may quickly force fluid into lines leading to a medical device or quickly expel unwanted air bubbles from the reservoir 116 by retracting the plunger threads 125 and repositioning the plunger shaft 121.

In other instances, the practitioner may desire more precise control over the position of the plunger shaft 121 (for example when displacing the plunger shaft 121 in order to adjust the fluid pressure within the reservoir 116) or it may simply be difficult or impossible without a mechanical advantage to displace the plunger shaft 121 due to high fluid pressure within the reservoir 116. In these instances, the practitioner may opt to displace the plunger shaft 121 by rotation of the plunger shaft 121.

Similar principles of operation of the inflation device 100 may be achieved with different configurations of the inflation device 100. For example, the coupling member 118 may be integrally formed with the syringe body 112. In that embodiment threads 111 and threads 117 may not be present. In another example, the coupling member 118 may be rotatably coupled to the syringe body 112, such as via a rotatable hub. In such embodiments, rotation of the coupling member 118 inserts or retracts the plunger 120 within the syringe body 112 when the plunger 120 is engaged with the coupling member 118. For example, the coupling member 118 may be rotated counter-clockwise while the plunger shaft 121 is rotated clockwise to advance the plunger 120. The coupling member 118 may comprise additional features, such as levers, to facilitate mechanical advantage in the rotation of the coupling member 118.

In the illustrated embodiment, the inflation device 100 is configured to provide a mechanical advantage when engaging or disengaging the coupling member 118. Referring back to FIG. 3, the handle 130 of the inflation device 100 may include components that enable a practitioner to retract the thread rail 124 of the plunger 120. In some embodiments, the plunger shaft 121 is fixed to a first member such as an inner member 131 of the handle 130. The thread rail 124 may be fixed to a trigger 133 component of the handle 130. Further, a biasing component 135 may be configured to bias the trigger 133 in a distal direction. Because the trigger 133 is fixed to the thread rail 124, a distally oriented force on the trigger 133 will result in a distally oriented force on the thread rail 124 as well. The force provided by the biasing component 135 (hereafter referred to as the biasing force) may thus bias the thread rail 124 in the engaged position as described above. Conversely, overcoming the biasing force and translating the trigger 133 in a proximal direction with respect to the plunger shaft 121 and the inner member 131 may retract the plunger threads 125.

In some embodiments the handle 130 further includes a second member such as an outer sleeve 136 and one or more levers 140, 141. The levers 140, 141 may be disposed such that they provide mechanical advantage, enabling the user to more easily overcome the biasing force and draw the trigger 133 toward the inner member 131. Any configuration for providing mechanical advantage in operation of an inflation device, such as the configurations disclosed in U.S. Patent Publication No. 2013-0123693, the contents of which are incorporated herein by reference in their entirety, may be used with the inflation devices disclosed herein, with the aid of the present disclosure.

A handle configured to provide a mechanical advantage when retracting a thread rail may be desirable for certain therapies that require large syringes or high pressure. Such therapies may also require a larger biasing force due to the size of the device or the pressure within the device. A handle providing a mechanical advantage may make devices configured for such therapies easier to use.

In some embodiments, the handle 130 is not configured to provide a mechanical advantage when disengaging the coupling member 118. For example, the levers 140 and 141 may not be present. In such embodiments, a user may need to directly overcome the biasing force of the biasing component 135 to disengage the plunger threads 125 of the thread rail 124 from the coupling member threads 119.

Many design modifications relating to the outer sleeve 136 are within the scope of the current disclosure. For example, in the illustrated embodiments, the outer sleeve 136 has a cap-like shape, fitting over the inner member 131. In other embodiments, the outer sleeve 136 is designed as a button that slides into the inner member 131 when it is compressed. Likewise, any other longitudinally actuatable component may be utilized in place of the outer sleeve 136.

The handle mechanism described above, and shown in each of FIGS. 2 and 3, may also be utilized to change the location and direction of an input force required to retract the plunger threads 125. Essentially, the mechanism allows a user to draw the trigger 133 toward the inner member 131 (and thus retract the threads) solely by applying a distally oriented force to a top surface 138 of the outer sleeve 136. As outlined above, the levers 140, 141 transfer this force to the trigger 133, which retracts the plunger threads 125.

In some instances a user, such as a medical practitioner, may desire to displace the plunger 120 in a distal direction with only one hand. This may be accomplished by grasping the syringe body 112 and using a surface, for example a table top, to apply a distally oriented force on the top surface 138 of the outer sleeve 136. In this manner, a mechanism such as that described above may enable a practitioner to displace the plunger 120 in a one-handed fashion.

The sensor component 150 may comprise a housing 151 coupled to a mounting bracket 152 of the syringe body 112. The housing 151 may be configured to receive a sensor assembly 154 (FIG. 3). The sensor assembly 154 may comprise the pressure sensor 156 and the transmitter 158. The pressure sensor 156 may be configured to measure the pressure within the syringe body 112. In some embodiments, additional sensors may measure, temperature, volume displaced, and viscosity of fluid. The pressure sensor 156 may comprise any number of known pressure sensors. For example, the pressure sensor 156 may be a transducer. In some embodiments, the pressure sensor 156 measures gauge pressure, such that when pressure within the syringe body 112 drops below atmospheric pressure, then the gauge reads a negative pressure. Additionally, the pressure sensor 156 may be sealed such that the reference pressure does not change with changes in environmental atmospheric pressure. The pressure sensor 156 may be a force collector such as a piezoresistive strain gauge, a capacitive diaphragm, an electromagnetic diaphragm, or a potentiometric gauge.

The sensor assembly 154 may comprise a circuit board 155 having a top surface and a bottom surface. The sensor assembly 154 may further comprise one or more connection points configured to connect components of the sensor assembly 154 with other components of the inflation device 100, such as a battery 157.

The housing 151 may comprise an interior portion configured to receive the circuit board 155 and other components of the sensor assembly 154. In some embodiments, the circuit board 155 is configured to be just smaller than the interior portion, allowing the circuit board 155 to fit within the interior portion.

The circuit board 155 and other components of the sensor assembly 154 may be configured to be coupled to the housing 151. In some embodiments, the sensor assembly 154 is coupled to the housing 151 through a snap fit connection. As used herein, snap fit-type connections refer very broadly to a wide variety of fits or connections, such as connections that rely on friction between component parts (as opposed to adhesive or mechanical fasteners) to couple the component parts. In some embodiments, snap fit connections comprise a groove or slot in a first component, configured to receive a second component. One or more protrusions, tabs, ridges, ribs, barbs, or other locking feature may be disposed such that the feature is deformed when the second component is pushed into the receiving portion of the second component. Once the second component is in place, the locking feature may return to its initial position and lock the second component in place.

A wide variety of features (e.g., protrusions, tabs, ridges, barbs, slots, channels, holes, and so on) may be configured for use in connection with a snap fit. In embodiments wherein the sensor assembly 154 is configured to snap fit into the housing 151, mating features are found on both components, or features are only identifiable on one of the two components. Still further, in some embodiments protruding-type locking elements (e.g., barbs, ridges, and so on) are on either or both components and receiving-type locking elements (e.g., grooves, slots, and so on) are on either or both components.

FIG. 3 illustrates one embodiment of the circuit board 155 being disposed within the interior portion of the housing 151. The pressure sensor 156 may be coupled directly to the circuit board 155. An o-ring 159 is also shown in connection with this assembly. Each component of this assembly may be configured to be coupled together through use of one or more snap fit connections. As shown in FIG. 3, the circuit board 155 may be configured to exert pressure on the o-ring 159 when the components are assembled. In some embodiments, this pressure results from positional constraints on the circuit board 155 by the snap fit connection. FIG. 3 also illustrates how an aperture 112a may provide fluid communication with the pressure sensor 156 when the device is assembled. In such embodiments, the transmitter 158 may be located on the top surface of the circuit board 155.

As shown in FIG. 3, the pressure sensor 156 may be coupled to the bottom surface of the circuit board 155. The pressure sensor 156 may be configured to be in direct fluid communication with the interior portion of the syringe body 112. Thus, in some embodiments, no secondary fluid—such as a gel—is disposed between the pressure sensor 156 and the interior portion of the syringe body 112. A system configured for use without a gel or secondary fluid may remove the risk that inconsistencies (such as bubbles or leaks) in the secondary fluid will undesirably alter sensor measurements.

A seal, such as the o-ring 159, may be configured to isolate the pressure sensor 156 from the outside environment. In other words, the seal may be positioned such that the pressure sensor 156 is in fluid communication with the interior portion of the syringe body 112 but not with other areas of pressure. In the illustrated embodiment, the o-ring 159 is configured to be disposed around the aperture 112a such that the o-ring 159 seals the fluid communication between the pressure sensor 156 and the aperture 112a when the inflation device 100 is assembled. In some embodiments the circuit board 155 and housing 151 are configured to exert compressive forces on the o-ring 159 when the circuit board 155 and housing 151 are coupled. In some instances the receiving portion of a snap fit design is positioned such that the circuit board 155 and/or housing 151 partially compress the o-ring 159 in order to be snapped into place.

Alternatively, the pressure sensor 156 may be coupled to the top surface of the circuit board 155 and a circuit board aperture provides communication between the bottom surface of the circuit board 155 and the pressure sensor 156. In such embodiments, the transmitter 158 may be located on the top surface of the circuit board 155 as well.

The sensor assembly 154 may further comprise a pull tab 160 configured to electrically isolate the battery 157 from the circuit board 155 when the pull tab 160 is in place. The pull tab 160 may be configured to be removable. The sensor assembly 154 may be configured to continuously transmit pressure data when the pull tab 160 is removed. It should be understood that in embodiments where the pressure sensor 156 is a digital sensor, then "continuously transmit" means to repeatedly transmit at a consistent interval. For example, the clock speed of a processor controlling the pressure sensor 156 may determine the frequency with which pressure data is collected by the pressure sensor 156.

As an alternative to a pull tab 160, the sensor assembly 154 may comprise an on/off switch configured to control conduction of electrical energy from the battery 157 to the circuit board 155. When the switch is in the "on" position, the sensor assembly 154 may be configured to continuously transmit pressure data. As a further alternative, the sensor assembly 154 may alternatively or additionally comprise a momentary switch. The momentary switch may be configured to transition sensor assembly 154 from a power save mode to a full power mode. The momentary switch may comprise a momentary button or trigger.

Figure 4:
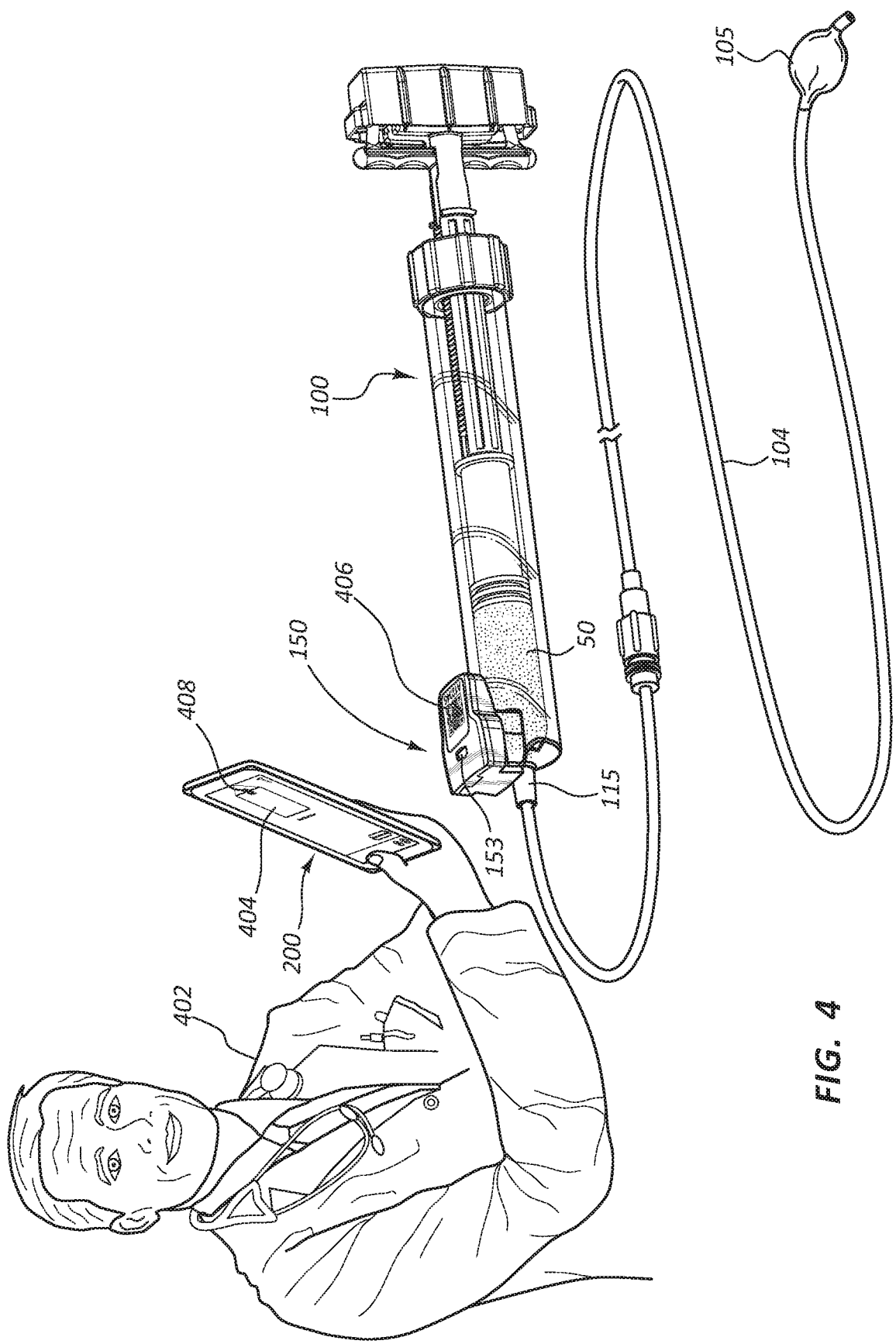
FIG. 4 illustrates an embodiment of an inflation system during pairing.

FIG. 4 illustrates an embodiment of an inflation system during pairing. In the illustrated embodiment, the inflation system comprises the inflation device 100 of FIG. 1 and a portable display device 200. In FIG. 4 the inflation device 100 of is being paired with the portable display device 200. The pairing procedure establishes a wireless communication link between the inflation device 100 and the portable display device 200.

The portable display device 200 may comprise a transceiver, a camera, a screen 404, and a processor. The transceiver may receive wireless signals from the inflation device 100. The signaling may include information for pairing or sensor data. The camera may capture a video feed, and the screen 404 may display the video feed.

In some embodiments, the pairing procedure may be initiated based on distance between the inflation device 100 and the portable display device 200. In an operation room with multiple inflation devices, a physician 402 may pair the portable display device 200 to a desired inflation device by moving the portable display device 200 within a threshold distance of the desired inflation device. Thus, pairing may be limited to the desired inflation device and no other inflation devices in the operating room. For example, in some embodiments, the inflation device 100 and the portable display device 200 must be within three to six inches from each other to initiate the pairing procedure.

The distance between the inflation device 100 and the portable display device 200 may be determined based on strength of a signal from the inflation device 100. For example, the physician 402 may remove a pull tab 160 from the sensor component 150 of the inflation device 100 to cause the sensor component 150 to begin sending a signal advertising a serial number for pairing. The portable display device 200 may measure the signal and determine a relative signal strength indicator (RSSI) for the signal. If the signal is higher than a threshold RSSI number, the portable display device 200 may determine that the inflation device 100 is in pairing distance. Upon determining that the inflation device 100 is in pairing distance, the portable display device 200 may initiate pairing.

To encourage the physician 402 to bring the portable display device 200 and the inflation device 100 within a threshold pairing distance, the portable display device 200 may have a visual marker 406 and the screen 404 of the inflation device 100 may overlay an alignment element 408 on the video feed. The alignment element 408 indicating a target position for the visual marker 406 on the inflation device 100 relative to the portable display device 200 to initiate a pairing procedure. For example, the alignment element 408 may include a frame, and for alignment a user positions the camera such that images of the visual marker 406 on the inflation device 100 are within the frame on the portable display device 200. When the visual marker 406 is aligned, the portable display device 200 may pair with the inflation device 100. The alignment causes the portable display device 200 and the inflation device 100 to be within a threshold pairing distance where the threshold signal strength is exceeded.

In some embodiments, the portable display device 200 is further to perform operations to determine a size for the alignment element 408 based on features of its camera and the threshold distance or distance. For example, the lens aperture of the camera and a sensor size of the camera may be used to determine a field of view. The field of view may be used to calculate the distance and determine the alignment element 408 size to obtain a threshold signal strength.

In some embodiments, the visual marker 406 comprises a machine-readable optical label (e.g., barcode, QR code, etc.). Thus, the physician 402 may attempt to scan the optical label using the camera. In some embodiments, the orientation and positioning of the portable display device 200 during an attempted scan of the optical label may cause the threshold RSSI to be surpassed. In some embodiments, the optical label may not be actually scanned by the portable display device 200. In other embodiments, the optical label may contain information that the portable display device 200 may use to obtain information about the portable display device 200. For example, the portable display device 200 may verify a serial number of the connected inflation device 100 using the optical label. In some embodiments, if the optical label is not readable, the portable display device 200 can disregard information from the optical label or prompt user to check the serial number of the inflation device 100 to verify proper pairing.

In some instances, the user may not be successful in connecting the inflation device 100 and portable display device 200 using that information. Thus, in some instances, a user may manually begin a connection sequence. In some instances, for example, the portable display device 200 may be coupled to computer-readable memory that has information (e.g., connection information, operating parameters, etc.) related to the inflation device 100 or an attached medical device (e.g., a balloon). A user may select the inflation device or medical device from a menu on the portable display device 200 to access the information and connect the devices.

Connection may be established through proximity pairing while a user is simultaneously attempting to pair the inflation device 100 to the portable display device 200 through another method. For example, a proximity pairing function may be active on the inflation device 100 and/or the portable display device 200 as a user is attempting to pair the devices using the camera or a manual technique.

In connection with any pairing technique, an indicator light 153 may be used to indicate a pairing state of the inflation device 100. The indicator light 153 may comprise a light emitting diode (LED) that indicates an off state is indicated by being off. In an advertising state the LED may be flashing. In a paired state the LED may be solid. In an error state the LED may flash faster than when in the advertising state. Other LED states, or use of other indicators, to indicate these states is within the scope of this disclosure.

Figure 5:
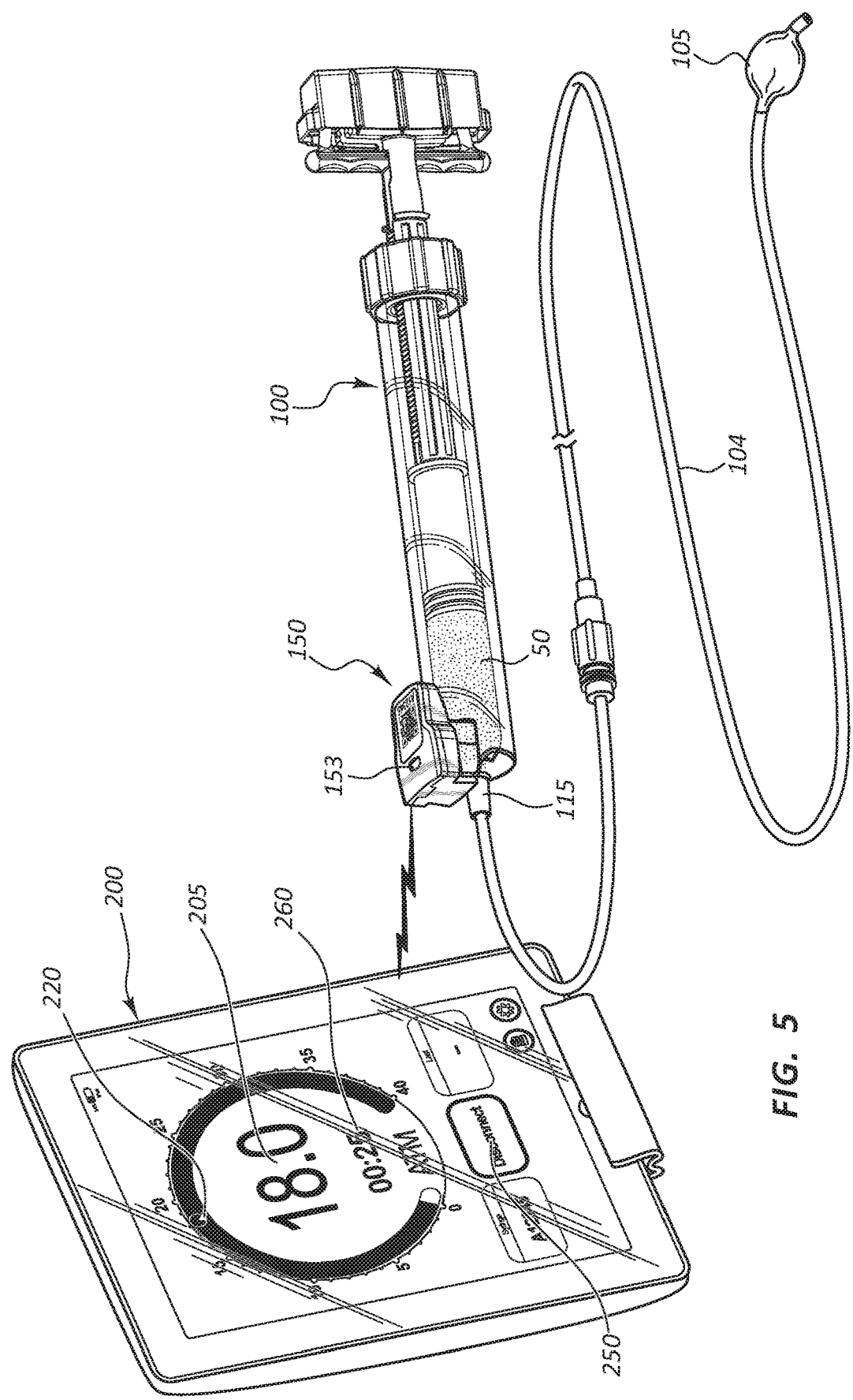
FIG. 5 is a perspective view of the inflation device of FIG. 1 with fluid disposed within the inflation device and a balloon coupled to the inflation device and a portable display device displaying the pressure within the inflation device.

FIG. 5 illustrates an embodiment of an inflation system in use (without the user present). In the illustrated inflation system, the inflation device 100 of FIG. 1 is coupled via a line 104 to a balloon 105. The syringe body 112 is filled with a fluid 50 for pressurizing the balloon 105. In the illustrated embodiment, the sensor component 150 is communicating with the portable display device 200.

The portable display device 200 may be configured to display a numeric pressure data 205, for example, such as the 30.0 ATM illustrated in FIG. 5, the 0.0 ATM illustrated in FIG. 6A, the 30.0 ATM illustrated in FIG. 6B, or the −5.0 ATM illustrated in FIG. 6C. The numeric pressure data 205 may comprise a current inflation pressure of the fluid 50. In some embodiments the portable display device 200 may be configured to display pressure readings in general terms, or within certain increments. For example, the gauge may display pressure in increments of 5 ATM (e.g., 0-5, 5-10, and 10-15 ATM). Continuous ranges for display as well as different increments are also within the scope of this disclosure.

The portable display device 200 may also be configured to display a non-numeric indication of pressure data, such as an arrow 220. The non-numeric indication of pressure data may indicate whether the current pressure is likely safe for the medical device attached to the inflation device, which in the illustrated embodiment is the balloon 105 and the inflation device 100, respectively. For example, in FIG. 6A, if the arrow 220 is in a first region, then the pressure in the balloon 105 is unlikely to burst the balloon 105. The non-numeric indication of pressure data may indicate whether the current pressure is potentially unsafe for the medical device attached to the inflation device. For example, in FIG. 6A, if the arrow 220 is in a second region, then the pressure in the balloon 105 may be sufficient to burst the balloon 105. The non-numeric indication of pressure data may also indicate whether the current pressure is likely unsafe for the medical device attached to the inflation device. For example, in FIG. 6A, if the arrow 220 is in a third region, then the pressure in the balloon 105 is likely sufficient to burst the balloon 105. The regions may be color-coded to intuitively inform a user of the meaning of the different pressure regions. For example, the regions may be colored similar to the RPM (rotations per minute) gauge of an automobile. For example, the first region may be colored green, the second region may be colored yellow, and the third region may be colored red.

The portable display device 200 may also be configured to display additional non-numeric indications of pressure data, such as markers 230. In the illustrated embodiment, the markers 230 circumscribe the regions 242, 244, and 246. As the arrow 220 rotates along the regions 242, 244, and 246, the distance between the arrow 220 and the nearest marker 230 provides a user with a quick non-numerical sense of the current pressure.

The portable display device 200 may also be configured to display units 210 (FIGS. 6A-6C) listing the pressure units for the numeric pressure data 205. A user may be able to toggle to other pressure units, such as by touching the display units 210 when the portable display device 200 comprises a touchscreen.

The portable display device 200 may also be configured to display a clock 260 (FIG. 5) listing the elapsed time since the beginning of a medical procedure or an inflation sequence which comprises a portion of a medical procedure. The clock 260 may be configured to start when an inflation device begins transmitting a wireless signal or when a connect/disconnect button 250 is touched, as discussed in more detail below.

The portable display device 200 may also be configured to display a peak pressure (FIG. 5). The peak pressure may be the peak pressure from the most recent inflation of a medical device attached to an inflation device. For example, when a user is alternately inflating and deflating a medical device, and with each inflation increasing the pressure relative to the prior inflation, then having a ready display of the prior peak pressure may be useful.

Figure 6:
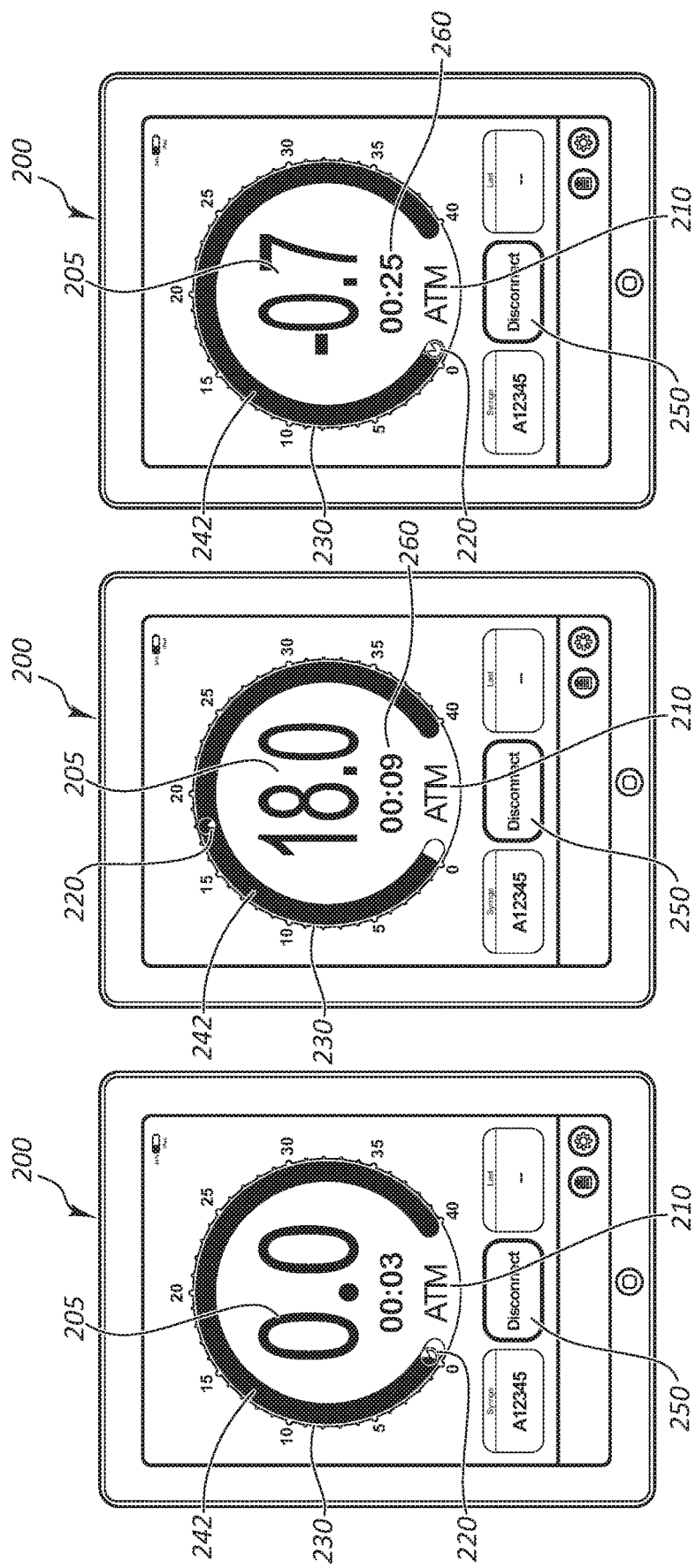
FIG. 6A is a front view of the portable display device of FIG. 5 displaying pressure within the inflation device of FIG. 1 before the start of a medical procedure.
FIG. 6B is a front view of the portable display device of FIG. 5 displaying a current pressure within the inflation device of FIG. 1 and the time lapsed since the start of a medical procedure, as shown during a medical procedure.
FIG. 6C is a front view of the portable display device of FIG. 5 displaying a negative pressure within the inflation device of FIG. 1 and the time elapsed since the start of a medical procedure, as shown during a medical procedure.

The portable display device 200 may comprise a handheld computer, such as a tablet computer with a touchscreen graphic user interface. Examples of such a tablet computer include, but are not limited to, an iPad or an Android tablet. In the touchscreen embodiments, the portable display device 200 may also be configured to display the connect/disconnect button 250, such as illustrated in FIGS. 5-6C. An inflation device, such as the inflation device 100, may be configured to continuously transmit pressure data. In some instances, the portable display device 200 may be configured to only process the transmitted data after the connect/disconnect button 250 has been touched by a user. The portable display device 200 may be configured such that a user can initiate a connection (for example pair the portable display device 200 and an inflation device via Bluetooth) through interaction with one or both components. For example, when the portable display device 200 is not connected to an inflation device, then the connect/disconnect button 250 may display "connect." When a user touches the "connect" button 250, then the portable display device 200 may initiate an algorithm to search for wireless signals generated by medical devices, such as inflation devices. By contrast, when the portable display device 200 is connected to an inflation device and is receiving and processing the wireless transmission data, then the connect/disconnect button 250 may display "disconnect." When a user touches the "disconnect" button 250, then the portable display device 200 may stop processing wireless signals from the inflation device.

In some instances, the inflation device 100 may be configured with an indicator configured to communicate the connection status of the inflation device 100. For example, in FIG. 4, the indicator light 153 is coupled to the sensor component 150. This indicator light 153 may comprise an LED or other light, or may comprise a mechanical indicia, such as an arrow or other member disposed in a particular orientation when the inflation device 100 is connected. In some instances multiple LED lights may be used. For example, the indicator light 153 may emit red light when the inflation device 100 is powered but not connected and green light when the inflation device 100 is connected with (for example, wirelessly paired with) the portable display device 200.

The portable display device 200 may be configured to display pressure data associated with prior inflations of the inflation device 100 for a particular patient.

The portable display device 200 may be configured to transmit pressure data to a computer that stores patient data. The transmission may be via any number of known transmission means. For example, the transmission may be via email or a file transfer protocol or may be via a standardized medical records protocol. An example of a standardized medical protocol is HL7 v3.0. For the sake of clarity, it should be understood the portable display device 200 may receive a wireless signal, such as a Bluetooth signal, from the transmitter of an inflation device, convert that signal into pressure data, and then transmit the pressure data via a wireless signal, such as a Wi-Fi signal, to a server (such as a cloud server) that stores patient data.

In some embodiments, the pressure data may interface with a charting system. The portable display device 200 may be configured to integrate pressure data from the inflation device 100 into a patient's medical records. The portable display device 200 may also be configured to connect with a printer and print pressure data transmitted by the inflation device 100.

The portable display device 200 may be configured to toggle the display of the pressure data between different pressure units.

The portable display device 200 may be configured to receive input of patient information associated with the pressure data.

The portable display device 200 may be configured to receive input of a medical device type to be inflated by the inflation device 100, such as a medical balloon. In some embodiments, the portable display device 200 is configured to allow selection of a type of medical balloon to be inflated by the inflation device 100. The portable display device 200 may be connected to computer-readable memory storing information regarding various inflation devices, such as balloons. A user may select a particular device from a menu on the portable display device 200 and/or read a bar code or QR code using a camera or other reader on the portable display device 200, portable display device 200 could then access the appropriate stored data. This data may be stored remotely and accessed via a network.

In some embodiments, selection of a specific balloon may be configured to alter the graphic displayed by the portable display device 200. For example, in FIGS. 6A-6C, the markers 230 denote approximately 1 ATM increments of pressure. However, if a medical balloon is selected on the portable display device 200 that has a maximum pressure of 100 psi, then each of the markers 230 may be configured to represent 20 psi increments of pressure. The arrow 220 would then move further around the regions 242, 244, and 246 at lower pressures as compared to the scale illustrated in FIGS. 6A-6C.

The portable display device 200 may be configured to allow illumination of the display of the pressure data in low-light or no-light settings. The illumination may be adjusted by a user, or, in some embodiments, the portable display device 200 may utilize a camera to detect light levels in the room and adjust illumination accordingly.

The portable display device 200 may be configured to provide audible signals when a desired maximum inflation is reached and/or audible signals as predetermined pressure levels are reached. The portable display device 200 and/or a connected processor may be configured to record and/or display the inflation history during a procedure. In some instances, a medical device may be configured to follow a particular inflation sequence over time. The portable display device 200 could display the desired sequence and track the actual progress along the sequence in real time. Additionally, the portable display device 200 could be configured to audibly call out inflation data, using voice or speech synthesis. For some procedures, this could reduce errors or mistakes that may be made when an operator vocally calls out data to another individual who records the data. In some instances the data call out could be automatic, for example, the portable display device 200 may be configured to call out inflation data following a particular input, for example, several seconds after a user pulls negative pressure to deflate a balloon, the portable display device could call out the peak inflation pressure preceding the deflation.

The portable display device 200 may be configured to respond to voice commands from a user of the inflation device 100 to perform a function of the portable display device 200. For example, a user may use voice commands to have the portable display device 200 initiate a search for inflation devices transmitting wireless signals in the vicinity of the portable display device 200 or change illumination. Any of the functions of the portable display device 200 discussed herein may be activated or deactivated by voice commands.

Figure 7:
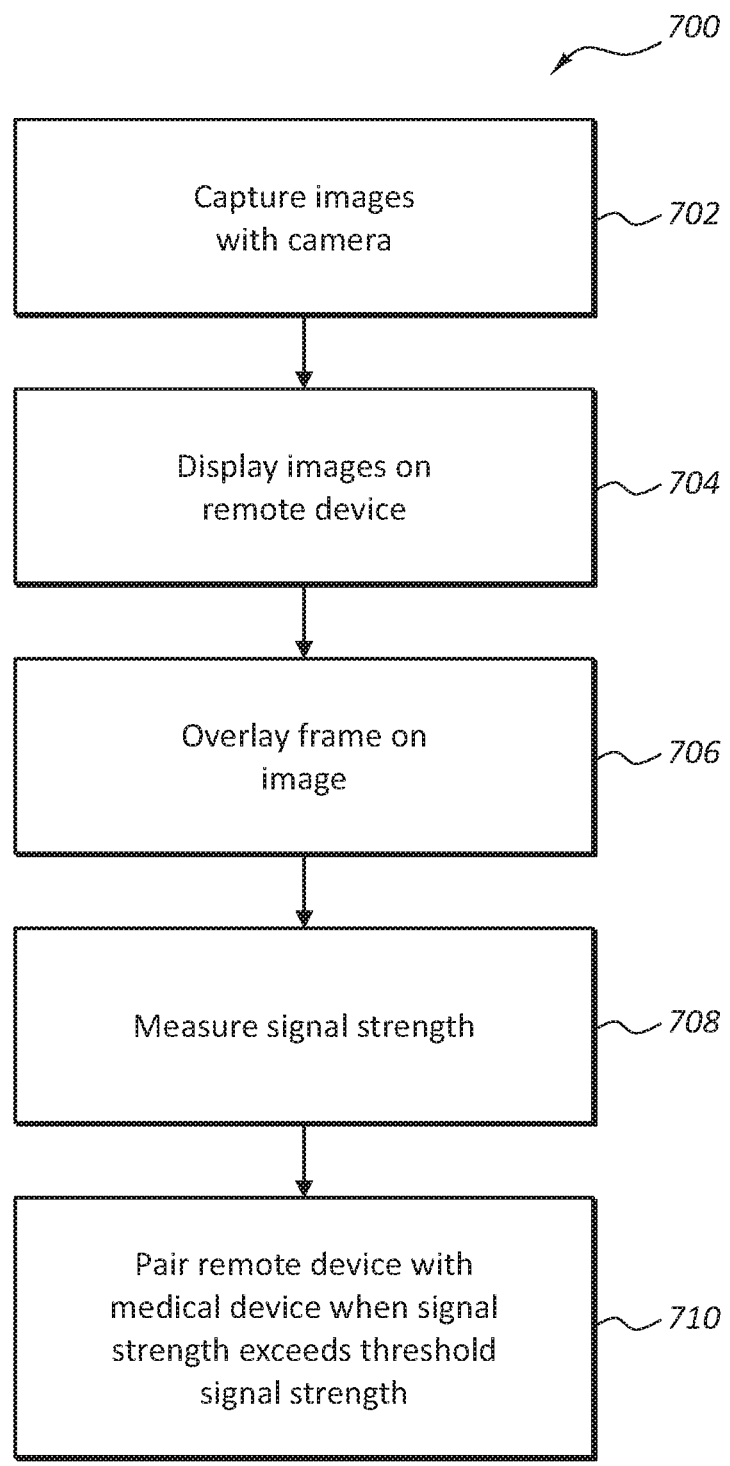
FIG. 7 illustrates a flow chart of one embodiment of a method of wirelessly coupling a remote display device to a medical device.

FIG. 7 illustrates a flow diagram 700 of a method for wirelessly coupling a remote display device to a medical device. In the illustrated embodiment, the method begins with capturing 702 an image stream with a camera associated with the remote display device. The image stream is displayed 704 on a remote device. The method further includes overlaying 706 a frame on the image stream for alignment of the remote display device with to the medical device for pairing. In some embodiments, for alignment a user positions the camera such that images of visual indicator on the medical device are within the frame on the remote display device. The remote display device may measure 708 a signal from the medical device to determine a signal strength. The remote display device may pair 710 with the medical device when the signal strength exceeds a threshold signal strength. In some embodiments, alignment of the visual indicator within the frame causes the medical device to be positioned such that the threshold signal strength is exceeded.

The method may further comprise additional steps before, after, and/or in between the steps the illustrated steps. For example, the method may further comprise determining a received signal strength indicator. Additionally, procedures within the scope of this disclosure do not necessarily comprise every listed step, rather procedures only comprising a portion of the steps illustrated in FIG. 7 are also within the scope of this disclosure.

In some embodiments, the medical device comprises an inflation device.

Additional steps may also comprise receiving a wireless signal representative of a pressure measured by a pressure sensor on the medical device, and displaying the pressure on the remote display device.

Additional steps may also comprise storing the pressure measured by the pressure sensor on a remote server.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware.

Accordingly, the various components, modules, systems, and/or features described herein may be embodied as modules within a system. Such a system may be implemented in software, firmware, hardware, and/or physical infrastructure. Although not always explicitly named herein, a module may be identified (named) based on a function it performs. For example, a module that is configured to display something may comprise specific hardware, software, or firmware and be properly referred to as a "display module."

Embodiments may also be provided as a computer program product including a non-transitory machine-readable medium having stored thereon instructions that may be used to program, or be executed on, a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions. Moreover, a computer program product may be run, executed, downloaded, and/or otherwise used locally or remotely via a network.

FIG. 8 illustrates an inflation device 100 used with two remote display devices (e.g., the portable display device 200, and a control display device 854). The portable display device 200 and the control display device 854 may both display the data from a sensor of a medical device. For example, in the illustrated embodiment, both the portable display device 200 and the control display device 854 may display a numeric pressure data 205 from the sensor component 150 of the inflation device 100.

During procedures a first individual 802 may monitor the pressure in an operating room 800 and a second individual 852 may monitor also monitor the pressure in a control room 850. The two displays may assist in charting the process and procedure. This could cut down on errors or mistakes that may be made when an operator vocally calls out data to another individual who records the data.

In some embodiments, the portable display device 200 receives data from the sensor component 150 and sends the data to the control display device 854. For example, the portable display device 200 may pair with the inflation device 100 based on proximity to form a first wireless communication link. The portable display device 200 may receive sensor data over a Bluetooth, Wi-Fi, or other wireless standard. The control display device 854 may also pair with the portable display device 200 to form a second wireless communication link. The second wireless communication link may be through Bluetooth, Wi-Fi, or other wireless standard.

In some embodiments, the portable display device 200 and the control display device 854 may both receive the wireless signal representative of data from the sensor component 150. The control display device 854 may be paired to the inflation device 100 based on proximity just as the portable display device 200 pairs with the inflation device 100. In some embodiments, the portable display device 200 initially pairs with the inflation device 100 based on proximity, and then the control display device 854 receives pairing information from the portable display device 200 for the inflation device 100 to initiate pairing between the control display device 854 and the inflation device 100.

The portable display device 200 and the control display device 854 may be interchangeable. For example, in some embodiments both of the portable display device 200 and the control display device 854 may be tablets, and either one may be used in the control room 850 or the operating room 800. This may allow for the control display device 854 to serve as a backup display for the portable display device 200. For instance, if the portable display device 200 fails, the first individual 802 may use the control display device 854 to finish a procedure.

Figure 9:
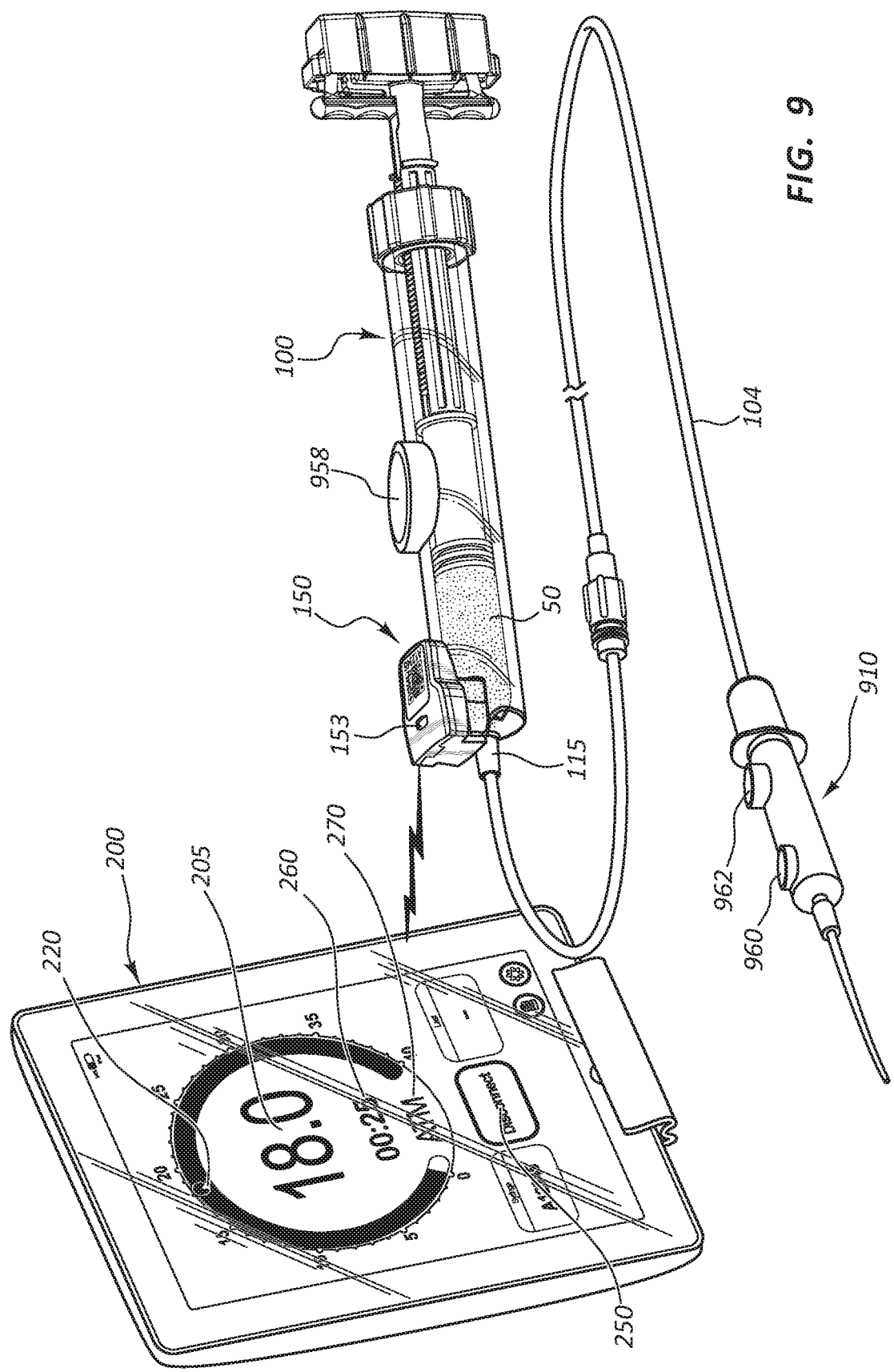
FIG. 9 illustrates an embodiment of an inflation system coupled to a bone cement syringe.

FIG. 9 illustrates an embodiment of an inflation system coupled to a bone cement device 910. As illustrated, an inflation device 100 may be used for fluid (e.g., bone cement) delivery. To assist in fluid delivery a plurality of sensors may be used (e.g. a pressure sensor 150, a volume sensor, 958, a temperature sensor 960, and a viscosity sensor 962). The sensors may be combined into a single sensor chip. In some embodiments, each sensor may be a discrete sensor device that is in communication with each other and/or the portable display device 200.

In some embodiment, sensors may be located on the bone cement device 910. For example, the temperature sensor 960 (e.g., thermocouple) may be used to measure the temperature of bone cement in the bone cement device 910, and the viscosity sensor 962 may measure the viscosity of the bone cement. This data may assist a physician in determining cement drying parameters.

The volume sensor 958 may track displacement of a pressurization component to determine an amount of liquid displaced by the pressurization component. The sensors may be in communication with a transmitter configured to transmit a wireless signal representative of the pressure measured by the pressure sensor 956, the temperature measured by the temperature sensor 960, the amount of liquid displaced measured by the volume sensor 958, and the viscosity measured by the viscosity sensor 962 to measure the viscosity of the liquid in the body.

Figure 10:
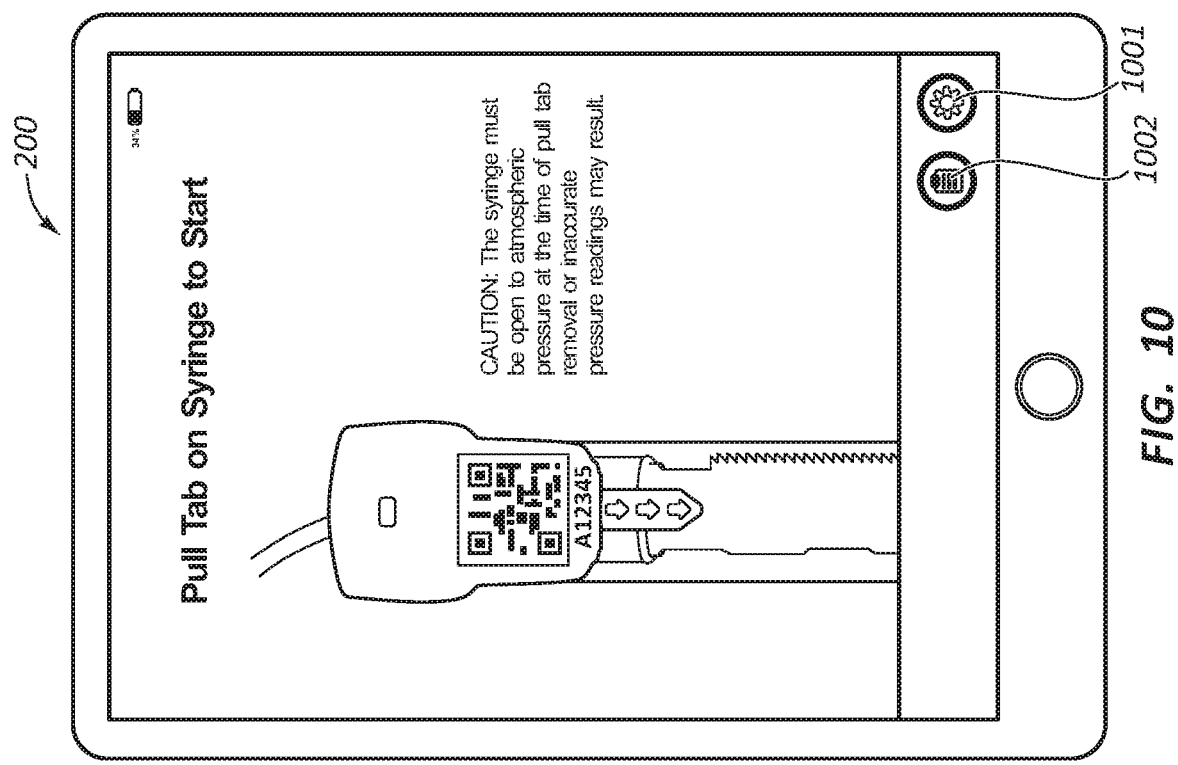
FIG. 10 is a front view of another embodiment of a portable display device in a first configuration.

FIG. 10 is a front view of another embodiment of the portable display device 200 in a first configuration. As shown, the portable display device 200, can be configured such that it initially displays information relative to the setup of an inflation device or system. For example, the portable display device 200 may indicate to a user how to power up a sensor component on an inflation device and/or how to begin wirelessly connecting the inflation device to the portable display device 200. Additionally, the portable display device 200 may include a settings icon 1001 or a history icon 1002 to display settings or inflation history of the system. Other features or icons could also be included.

In the state shown in FIG. 10, the portable display device 200 may be searching for devices to connect to, or may be configured to wait for user input to do so. In some instances, the portable display device 200 will automatically respond when an inflation device is activated or powered up within range of the portable display device 200 and prompt a user regarding connection to that device.

Figure 11:
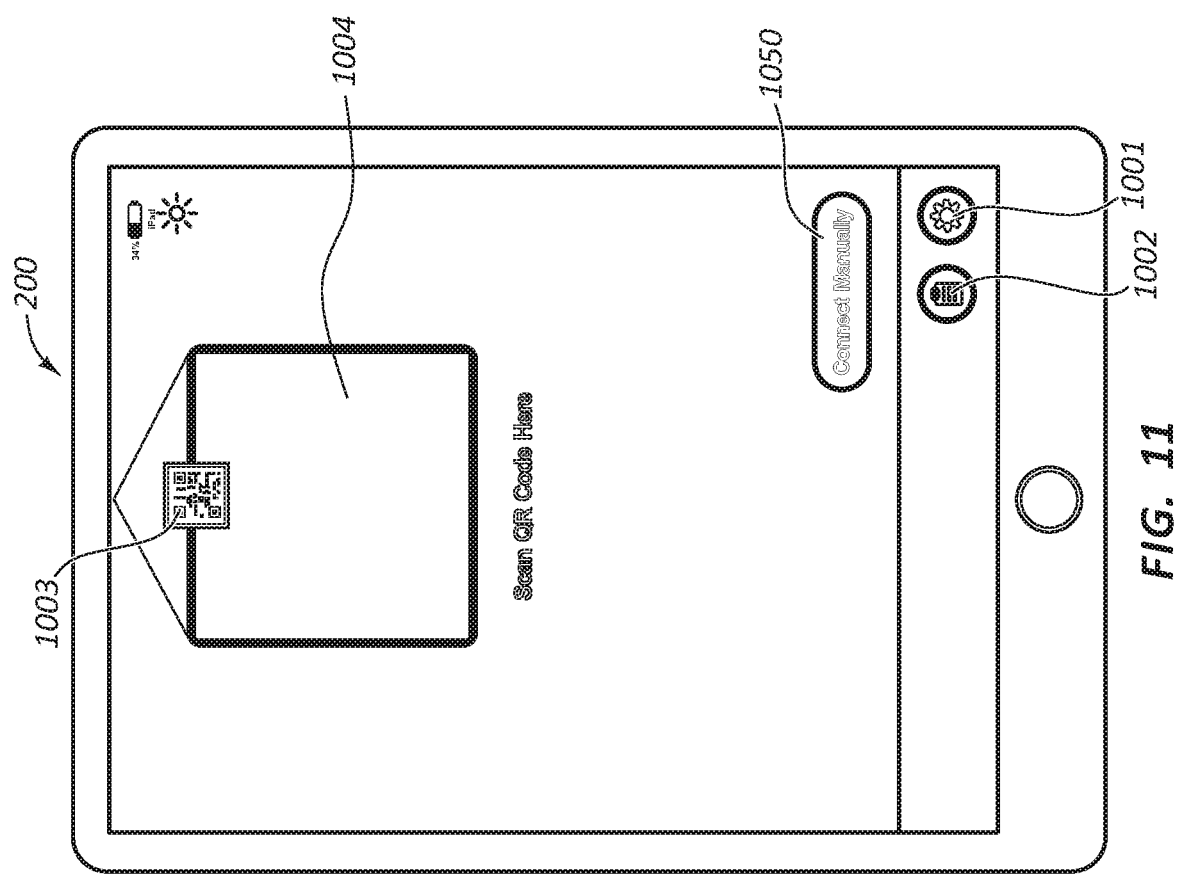
FIG. 11 is a front view of the portable display device of FIG. 10 in a second configuration.

As shown in FIG. 11, the portable display device 200 may be configured to aid in connecting the portable display device 200 to an inflation device or other medical device. For example, the portable display device 200 may automatically activate a camera on the portable display device 200 when an active inflation device is within range.

In the illustrated embodiment, a QR code icon 1003 is shown in this state to communicate to a user to position the camera such that an image of a QR code on the desired inflation device is relayed from the camera and shown in a viewing portion 1004 of the portable display device 200. In some embodiments, the QR code icon 1003 may not be scanned by the portable display device 200 for pairing. However, bringing the desired inflation device into a position to be shown in the viewing portion 1004 may cause the desired inflation device to be near enough to the portable display device 200 that a signal strength threshold is surpassed causing pairing to initiate. The same technique may be used with bar codes or other markings on the inflation device.

The portable display device 200 may further comprise a connect/disconnect button 1050. When the portable display device 200 is in the configuration of FIG. 10, the connect/disconnect button 1050 may be configured to override the camera/automatic connection and allow a user to manually connect an active device in range. For example, if no device is connected, activation of the connect/disconnect button 1050 may bring up a list or menu of all available devices within range. A user could then manually select the desired device.

Once a device is connected, the connect/disconnect button may change (e.g., change to "disconnect") to indicate the devices are connected (for example by Bluetooth pairing). An indicator on the inflation device (e.g., an LED) may also be configured to communicate that the devices are connected.

Figure 12:
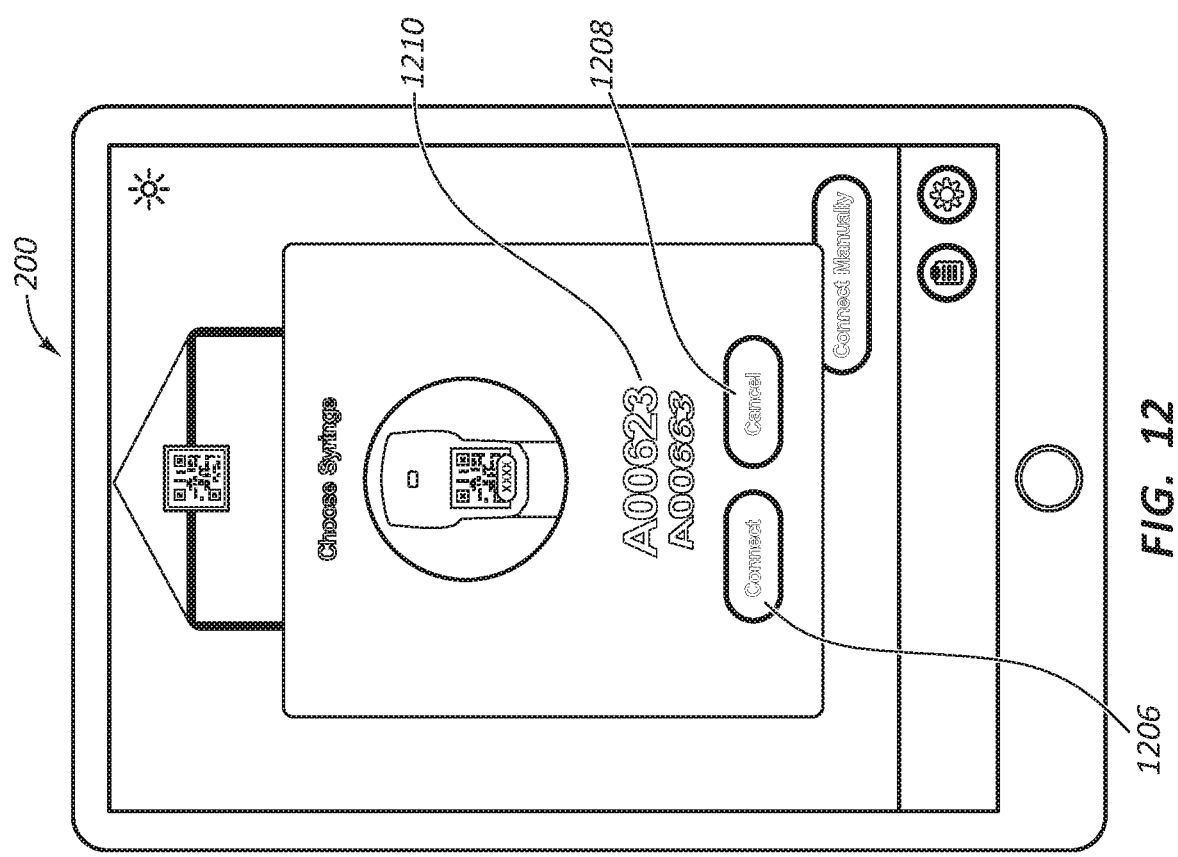
FIG. 12 is a front view of the portable display device of FIG. 10 in a third configuration.

FIG. 12 illustrates the portable display device 200 manually pairing with a syringe. The portable display device 200 may display a list of syringes 1210 within range. A user may select a connect button 1206 to connect with a selected syringe, or a cancel button 1208 to cancel manual pairing.

Figure 13:
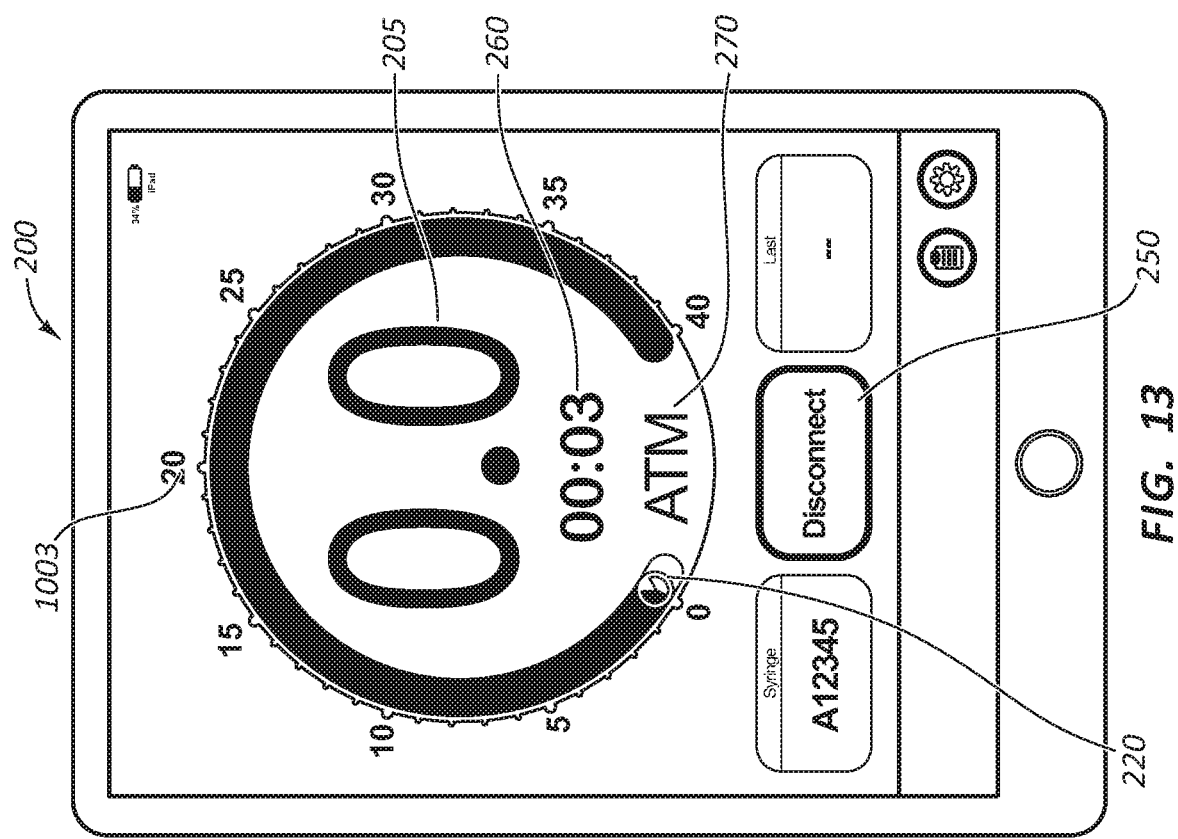
FIG. 13 is a front view of the portable display device of FIG. 10 in a fourth configuration.

In the configuration of FIG. 13, the portable display device 200 is wirelessly connected to an inflation device and information regarding the inflation device is shown in the portable display device 200. For example, the connect/disconnect button 250 indicates a device is connected. The portable display device 200 may display the numeric pressure data 205, display units 270, and non-numeric pressure data, such as by the arrow 220. Additionally, a portion of the portable display device 200 may display the clock 260 that tracks the inflation sequence or medical procedure. Additional portions of the portable display device 200 may indicate various information such as battery life, power connection status, and so forth.

In some embodiments, additional sensor data may be displayed on the portable display device 200. For example, a temperature, a viscosity of a liquid being dispensed, and a volume of liquid dispensed may be presented to a user. This information may be useful in determining delivery rate of the liquid. For instance, the portable display device 200 may use the time, temperature, pressure, and/or viscosity to determine a life window of bone cement.

Figure 14:
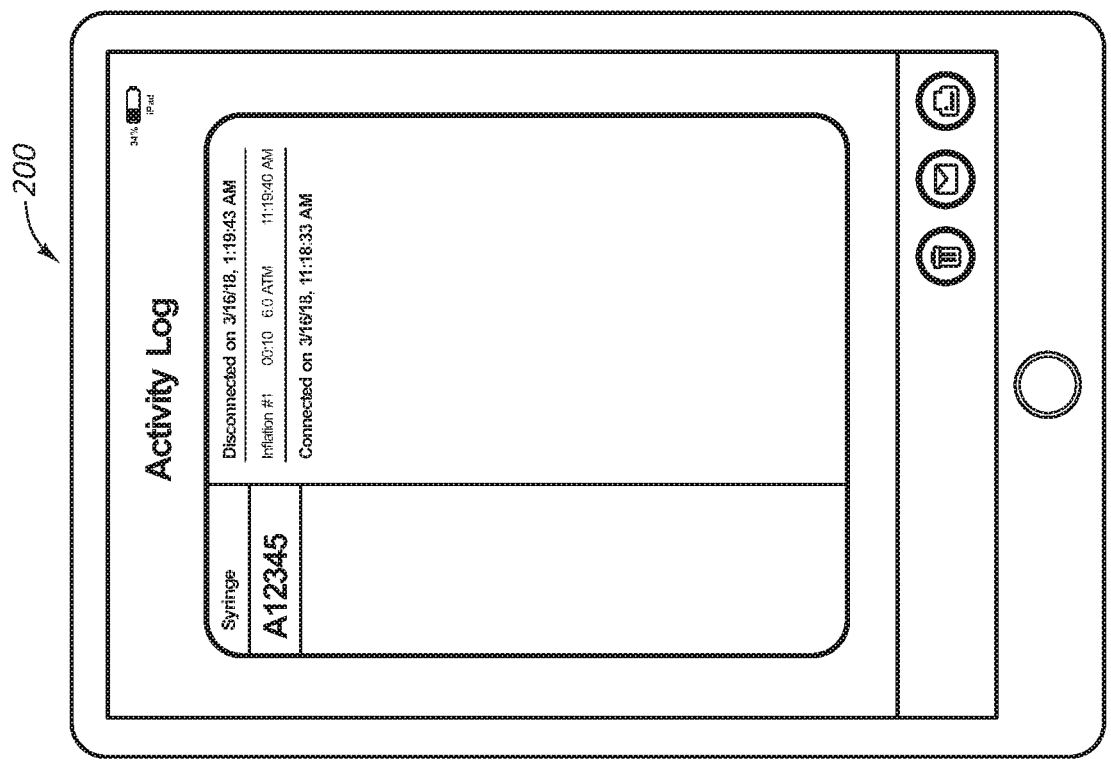
FIG. 14 is a front view of the remote display device of FIG. 10 in a fifth configuration.

In the configuration of FIG. 14, the portable display device 200 is displaying an activity log associated with the portable display device 200. The activity log may track the time, duration, peak pressure, and serial number of syringes used while paired with the portable display device 200. This may allow a user to review procedure data at a later time.

Figure 15:
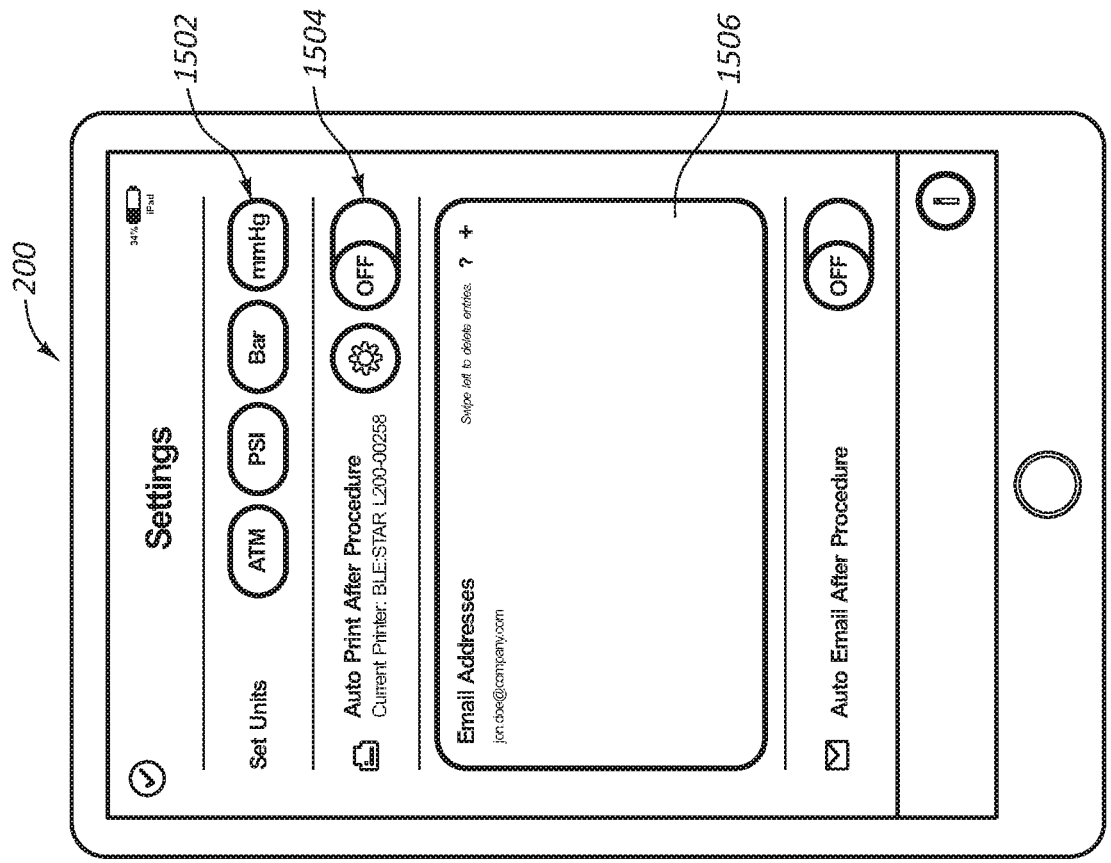
FIG. 15 is a front view of the remote display device of FIG. 5 in a sixth configuration.

In the configuration of FIG. 15, the portable display device 200 is displaying settings of the portable display device 200. A user may select a desired unit 1502 to be displayed during a procedure. Additionally, a user may select a print button 1504 to cause the procedure activity to be automatically printed after the syringe is disconnected.

In some embodiments, the procedure data may be sent to an email 1506 or a server. During or after a procedure, it is within the scope of this disclosure for the portable display device 200 to further transmit inflation data to an auxiliary device. For example, the portable display device 200 can send inflation data to a hospital computer, patient records, or other locations. The portable display device 200 can be configured to interact with standard hospital data storage components or computers. In some embodiments, the portable display device 200 can be configured to output data directly to existing or standard auxiliary devices, for example, by emulating an input device (e.g., a keyboard) for the existing device.

Without further elaboration, it is believed that one skilled in the art can use the preceding description to utilize the present disclosure to its fullest extent. The examples and embodiments disclosed herein are to be construed as merely illustrative and exemplary, and not as a limitation of the scope of the present disclosure in any way. It will be apparent to those having skill in the art that changes may be made to the details of the above-described embodiments without departing from the underlying principles of the disclosure herein. It is intended that the scope of the invention be informed by the claims appended hereto and their equivalents.

The invention claimed is:

1. A system for remotely displaying sensor data from a medical device, the system comprising:
 a medical device with a visual marker; and a first remote display device comprising:
  a transceiver to receive a wireless signal from the medical device; a camera to capture a video feed;
  a screen; and
  a processor to perform operations to:
   display, on the screen, the video feed;
   overlay an alignment element on the video feed, the alignment element indicating a target position for the visual marker on the medical device to be disposed within to initiate a pairing procedure;
   measure a signal strength of the wireless signal; and
   pair the first remote display device with the medical device when the signal strength exceeds a threshold signal strength, wherein the threshold signal strength is exceeded when the visual marker on the medical device is in the target position.

2. The system of claim 1, wherein the medical device comprises a pressure sensor, and a transmitter in communication with the sensor and configured to transmit a wireless signal representative of data from the sensor.

3. The system of claim 2, the processor is further to perform operations to display the data from the sensor.

4. The system of claim 3, further comprising a second remote display device to display the data from the sensor.

5. The system of claim 4, wherein the first remote display device sends the data from the sensor to the second remote display device.

6. The system of claim 4, wherein the first remote display device and the second remote display device receive the wireless signal representative of data from the sensor.

7. The system of claim 4, wherein the second remote display device receives pairing information associated with the medical device from the first remote display device to facilitate pairing of the second remote display device with the medical device.

8. The system of claim 1, wherein the processor is further to perform operations to determine a size for the alignment overlay based on a lens aperture of the camera, a sensor size of the camera, and the threshold signal strength.

9. The system of claim 1, wherein the medical device further comprises a light emitting diode (LED) to indicate a state of the medical device,
wherein an off state is indicated by the LED being off, an advertising state is indicated by the LED flashing, a paired state is indicated by the LED being solid, and an error state is indicated by the LED flashing faster than when in the advertising state.

10. The system of claim 1, wherein the visual marker comprises a machine-readable optical label.

11. The system of claim 10, wherein the processor is further to perform operations to scan the machine-readable optical label to obtain information about the first remote display device.

12. The system of claim 1, wherein the medical device comprises a temperature sensor.

13. The system of claim 1, wherein the medical device comprises:
a body component;
a pressurization component configured to increase or decrease pressure within the body component by displacing the pressurization component with respect to the body component;
an actuator operably connected to the pressurization component and configured to displace the pressurization component with respect to the body component; and
a sensor that tracks displacement of the pressurization component to determine volume of a liquid displaced by the pressurization component.

14. A method for wirelessly coupling a remote display device to a medical device, the method comprising:
capturing an image stream with a camera associated with the remote display device;
displaying the image stream on the remote display device;
overlaying an alignment frame on the image stream for alignment of the remote display device with to the medical device for pairing, wherein for alignment a user positions the camera such that images of a visual indicator on the medical device are within the alignment frame on the remote display device;
measuring a signal from the medical device with the remote display device to determine a signal strength; and
pairing the remote display device with the medical device when the signal strength exceeds a threshold signal strength, wherein alignment of the visual indicator within the alignment frame causes the medical device to be positioned such that the threshold signal strength is exceeded.

15. The method of claim 14, wherein the visual indicator comprises a quick response code.

16. The method of claim 14, wherein measuring the signal comprises determining a received signal strength indicator.

17. The method of claim 14, further comprising:
receiving a wireless signal representative of a pressure measured by a pressure sensor on the medical device; and
displaying the pressure on the remote display device.

18. The method of claim 17, further comprising storing the pressure measured by the pressure sensor on a remote server.

19. An inflation device configured for use with a medical device, the inflation device comprising:
a body component configured to house a bone cement;
a pressurization component configured to increase or decrease pressure within the body component by displacing the pressurization component with respect to the body component;
an actuator operably connected to the pressurization component and configured to displace the body component;
a pressure sensor in communication with the body component and configured to measure pressure within the body component;
a temperature sensor configured to measure a temperature of the bone cement in the body component;
a volume sensor that tracks displacement of the pressurization component to determine an amount of bone cement displaced by the pressurization component; and
a transmitter in communication with the pressure sensor, the temperature sensor, and the volume sensor, the transmitter configured to transmit a wireless signal representative of the pressure measured by the pressure sensor, the temperature measured by the temperature sensor, and the amount of bone cement displaced measured by the volume sensor to a remote display device that is configured to determine a life window of the bone cement based on the transmitted pressure, temperature, and amount of bone cement displaced.

20. The inflation device of claim 19, further comprising a viscosity sensor to measure the viscosity of the bone cement in the body component.

* * * * *